United States Patent
Lupold et al.

(10) Patent No.: US 9,458,473 B2
(45) Date of Patent: Oct. 4, 2016

(54) COMPOSITIONS AND METHODS FOR RETARGETING VIRUS CONSTRUCTS

(75) Inventors: Shawn Edward Lupold, Ellicott City, MD (US); Ping Wu, Baltimore, MD (US); Ronald Rodriguez, Glenwood, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/807,359

(22) PCT Filed: Jun. 29, 2011

(86) PCT No.: PCT/US2011/042331
§ 371 (c)(1),
(2), (4) Date: Aug. 13, 2013

(87) PCT Pub. No.: WO2012/006145
PCT Pub. Date: Jan. 12, 2012

(65) Prior Publication Data
US 2013/0315870 A1    Nov. 28, 2013

Related U.S. Application Data

(60) Provisional application No. 61/359,449, filed on Jun. 29, 2010.

(51) Int. Cl.
*C12N 15/86* (2006.01)
*C12N 15/10* (2006.01)
*C07K 14/005* (2006.01)

(52) U.S. Cl.
CPC ............ *C12N 15/86* (2013.01); *C07K 14/005* (2013.01); *C12N 15/1037* (2013.01); *C12N 2710/10322* (2013.01); *C12N 2710/10343* (2013.01); *C12N 2710/10345* (2013.01); *C12N 2810/40* (2013.01); *C12N 2820/007* (2013.01)

(58) Field of Classification Search
None
See application file for complete search history.

(56) References Cited

U.S. PATENT DOCUMENTS 7,094,398 B1 * 8/2006 Lieber et al. ............... 424/93.2
7,297,542 B2 * 11/2007 Curiel et al. ................ 435/456

2003/0148520 A1    8/2003 Yu et al.
2003/0175245 A1    9/2003 Brough et al.
2004/0223949 A1   11/2004 Astsaturov et al.

OTHER PUBLICATIONS

Yoon, et al. (2003) "Random mutagenesis of the gene encoding a viral ligand for multiple cell entry receptors to obtain viral mutants altered for receptor usage", Proceedings of the National Academy of Science, USA., 101(49): 17252-57.*
Nishimoto, et al. (Feb. 19, 2009 online) "Oncolytic virus therapy for pancreatic cancer using the adenovirus library displaying random peptides on the fiber knob", Gene Therapy, 16: 669-80.*
Lim, et al. (2008) "Library Selection Approaches to Engineering Enhanced Retroviral and Lentiviral Vectors", Combinatorial Chemistry & High Throughput Screening, 11: 111-17.*
Wu, et al. (2010) "Adenovirus Targeting to Prostate-specific Membrane Antigen through Virus-displayed Semi-random Peptide Library Screening", Cancer Research, 70(23): 9549-53.*
Miura, et al., Gene Therapy, 2007, vol. 14, No. 20, pp. 1448-1460.
Lupold, et al., Reviews in Urology, 2005, vol. 7, No. 4, pp. 193-202.

* cited by examiner

*Primary Examiner* — Robert M Kelly
(74) *Attorney, Agent, or Firm* — Johns Hopkins Technology Ventures

(57) ABSTRACT

The present invention relates to the field of viral gene therapy. More specifically, the present invention provides compositions and methods for retargeting virus constructs. In one embodiment, the present invention provides an adenoviral construct comprising a nucleic acid encoding the peptide sequence MAE-X-PDP (SEQ ID NO:45), wherein X is an antigen targeting peptide. In a more specific embodiment, an adenoviral construct comprises a nucleic acid sequence encoding the peptide sequence MAEWQPDTAH-HWALTLPDP (SEQ ID NO:10) inserted into the HI-loop of adenovirus fiber protein. In yet another embodiment, the present invention provides a method for optimizing adenoviral infection of target cells comprising the steps of (a) generating a peptide-display adenovirus library, wherein the displayed peptide is a peptide that specifically binds an antigen expressed on the surface of a target cell, and wherein the displayed peptide is flanked by random peptide sequences; and (b) screening the peptide-display adenovirus library against the target cells.

5 Claims, 9 Drawing Sheets

FIG. 2. LIBRARY PEPTIDE SEQUENCES OF RANDOMLY SELECTED CLONES FROM EACH ROUND

| ROUND I | ROUND II | ROUND III | ROUND IV |
|---|---|---|---|
| PTPWQPDTAHHWATLPTR (SEQ ID NO:11) | PMNWQPDTAHHWATLTD (SEQ ID NO:12) | SPAWQPDTAHHWATLSSH (SEQ ID NO:13) | MAEWQPDTAHHWATLPDP (SEQ ID NO:10) |
| PPPWQPDTAHHWATLPNI (SEQ ID NO:14) | PETWQPDTAHHWATLGTP (SEQ ID NO:15) | SPAWQPDTAHHWATLSSH (SEQ ID NO:13) | MAEWQPDTAHHWATLPDP (SEQ ID NO:10) |
| YKPWQPDTAHHWATLSHQ (SEQ ID NO:16) | SPRWQPDTAHHWATLSP (SEQ ID NO:17) | TRPWQPDTAHHWATLPHT (SEQ ID NO:18) | MAEWQPDTAHHWATLPDP (SEQ ID NO:10) |
| TSPWQPDTAHHWATLSKR (SEQ ID NO:19) | SPRWQPDTAHHWATLSP (SEQ ID NO:17) | TRPWQPDTAHHWATLPHT (SEQ ID NO:18) | MAEWQPDTAHHWATLPDP (SEQ ID NO:10) |
| DKMWQPDTAHHWATLPF (SEQ ID NO:20) | NSRWQPDTAHHWATLTR (SEQ ID NO:21) | PSTWQPDTAHHWATLPHL (SEQ ID NO:22) | MAEWQPDTAHHWATLPDP (SEQ ID NO:10) |
| PSLWQPDTAHHWATLYPM (SEQ ID NO:23) | LAPWQPDTAHHWATLTDT (SEQ ID NO:24) | TSNWQPDTAHHWATLACT (SEQ ID NO:25) | MAEWQPDTAHHWATLPDP (SEQ ID NO:10) |
| NPSWQPDTAHHWATLKNQ (SEQ ID NO:26) | PTNWQPDTAHHWATLAPS (SEQ ID NO:27) | TSNWQPDTAHHWATLACT (SEQ ID NO:25) | MAEWQPDTAHHWATLPDP (SEQ ID NO:10) |
| SNYWQPDTAHHWATLPN- (SEQ ID NO:28) | CTNWQPDTAHHWATLKDS (SEQ ID NO:29) | GQSWQPDTAHHWATLEET (SEQ ID NO:32) | MAEWQPDTAHHWATLPDP (SEQ ID NO:10) |
| YNSWQPDTAHHWATLPTA (SEQ ID NO:30) | TREWQPDTAHHWATLDSS (SEQ ID NO:31) | GQSWQPDTAHHWATLEET (SEQ ID NO:32) | MAEWQPDTAHHWATLPDP (SEQ ID NO:10) |
| SGVWQPDTAHHWATLKTP (SEQ ID NO:33) | AGDWQPDTAHHWATLKAD (SEQ ID NO:34) | VHRWQPDTAHHWATLNRQ (SEQ ID NO:37) | MAEWQPDTAHHWATLPDP (SEQ ID NO:10) |
| SQTWQPDTAHHWATLPWP (SEQ ID NO:35) | GGPWQPDTAHHWATLPNS (SEQ ID NO:36) | EPTWQPDTAHHWATLDSE (SEQ ID NO:39) | MAEWQPDTAHHWATLPDP (SEQ ID NO:10) |
|  | PPKWQPDTAHHWATLPPP (SEQ ID NO:38) | EPTWQPDTAHHWATLDSE (SEQ ID NO:39) | MAEWQPDTAHHWATLPDP (SEQ ID NO:10) |
|  | PNVWQPDTAHHWATLPYP (SEQ ID NO:40) | AKDWQPDTAHHWATLDNV (SEQ ID NO:42) | MAEWQPDTAHHWATLPDP (SEQ ID NO:10) |
|  | EPCWQPDTAHHWATLPEI (SEQ ID NO:41) | AKDWQPDTAHHWATLDNV (SEQ ID NO:42) | MAEWQPDTAHHWATLPDP (SEQ ID NO:10) |
|  | PASWQPDTAHHWATLPQR |  |  |

FIG. 2

| ROUND I | ROUND II | ROUND III | ROUND IV |
|---|---|---|---|
| | (SEQ ID NO:43) | (SEQ ID NO:42) | (SEQ ID NO:10) |
| | PRPWQPDTAHHWATLPRQ (SEQ ID NO:44) | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |
| | | | MAEWQPDTAHHWATLPDP (SEQ ID NO:10) |

FIG. 2 CONTINUED

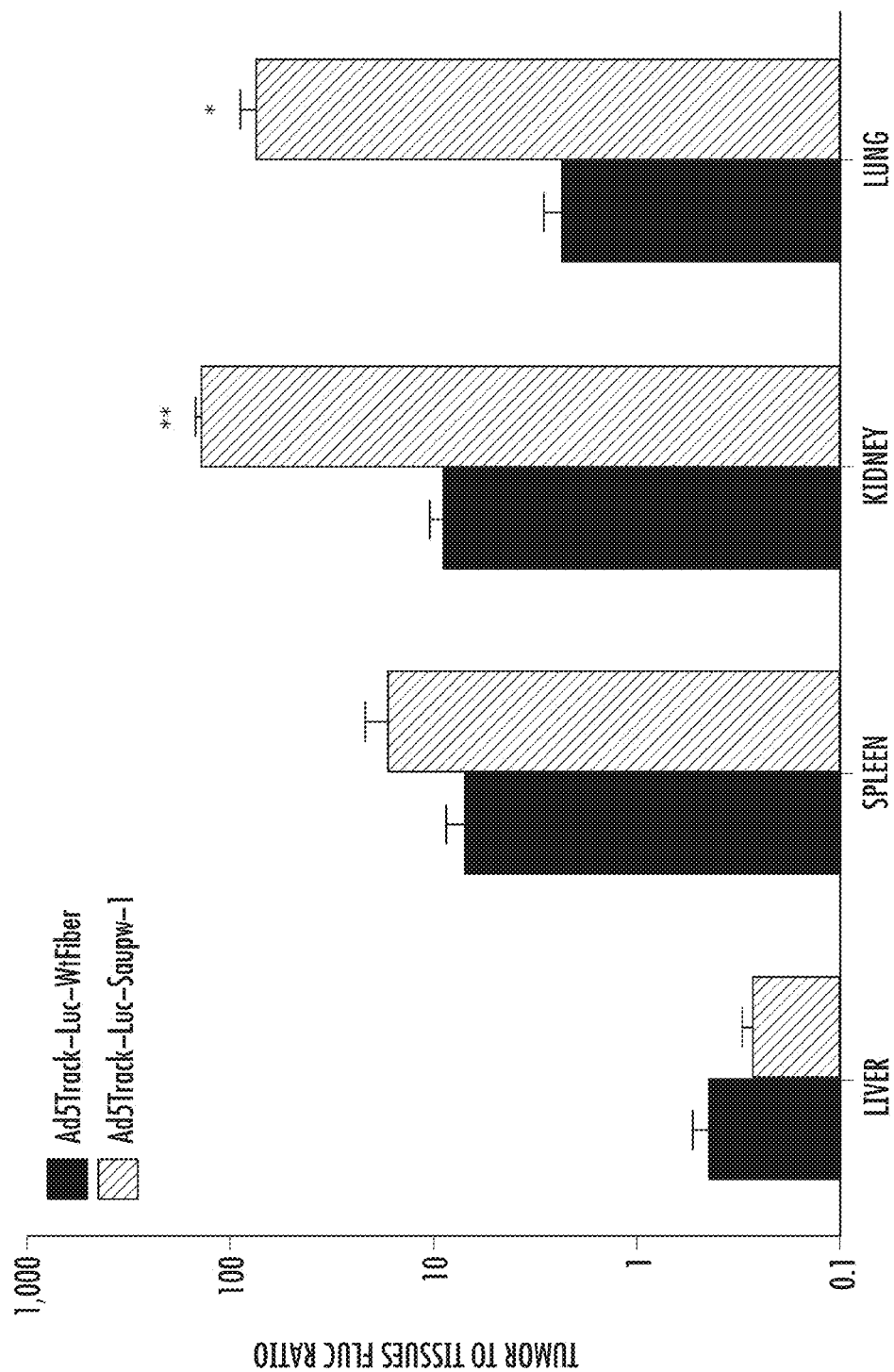

COMPOSITIONS AND METHODS FOR RETARGETING VIRUS CONSTRUCTS

CROSS-REFERENCE TO RELATED APPLICATIONS

This application is a 35 U.S.C. §371 U.S. national entry of International Application PCT/US2011/042331 having an international filing date of Jun. 29, 2011, which claims the benefit of U.S. Provisional Application No. 61/359,449, filed Jun. 29, 2010, the contents of each of the aforementioned applications are herein incorporated by reference in their entireties.

STATEMENT OF GOVERNMENTAL INTEREST

This invention was made with government support under grant no. CA121153, awarded by the National Institutes of Health. The government has certain rights in the invention.

FIELD OF THE INVENTION

The present invention relates to the field of viral gene therapy. More specifically, the present invention provides compositions and methods for retargeting virus constructs.

INCORPORATION-BY-REFERENCE OF MATERIAL SUBMITTED ELECTRONICALLY

This application contains a sequence listing. It has been submitted electronically via EFS-Web as an ASCII text file entitled "P11155-03_ST25.txt." The sequence listing is 14,352 bytes in size, and was created on Dec. 23, 2014. It is hereby incorporated by reference in its entirety.

BACKGROUND OF THE INVENTION

Cancer-fighting adenoviral vectors are now clinically available for intratumoral injection. However, the translation of this approach to the systemic treatment of metastatic tumors requires solutions to multiple obstacles including broad viral tropism, liver sequestration, hepatic toxicity, low-level coxsackie and adenovirus receptor (CAR) expression in some tumor types, and host immunity. See Barry et al., 11 CURR. OPIN. MOL. THER. 411-20 (2009); and Waehler et al., 8 NAT. REV. GENET. 573-87 (2007). Some of these problems have been overcome by genetically targeting the therapeutic effect through tissue-specific promoters or oncolytic mechanisms. For example, the first tissue-specific lytic adenovirus was developed for the treatment of prostate cancer (PCa) by limiting viral replication to cells containing activated androgen receptor. Rodriguez et al., 57 CANCER RES. 2559-63 (1997). These prostate-selective lytic vectors have been evaluated in clinical trials both as direct tumor injected agents and as systemically administered virus for castration-resistant metastatic PCa. Lipoid et al., 3 CANCER THER. 267-84 (2005). Although the therapeutic effect was limited to prostatic cells, the efficacy as a systemic therapy was hampered by viral sequestration and clearance. This reflects the loss of more than 90% of intravenously administered adenovirus through liver sequestration. Shashkova et al., 17 MOL. THER. 2121-30 (2009). Next generation cancer gene therapy vectors seek to enhance efficacy through capsid modifications designed to limit viral clearance and/or improve tumor infection through alternative receptors.

SUMMARY OF THE INVENTION

The present invention is based, in part, on the discovery that adenovirus-displayed, semi-random peptide libraries, in the form of flanking cassettes, can be applied to rescue the targeting ability of phage-derived peptides that were previously ineffective in such a complex environment. The result is a genetically modified adenovirus that successfully infects prostatic cells and tumors through PSMA. This approach can be applied to develop targeted agents for prostate cancer, or other cancers, not only in adenovirus but also in other experimental therapeutic platforms.

Accordingly, in one aspect, the present invention relates to the field of viral gene therapy. More specifically, the present invention provides compositions and methods for retargeting virus constructs. In one embodiment, the present invention provides an adenoviral construct comprising a nucleic acid encoding the peptide sequence MAE-X-PDP (SEQ ID NO:45), wherein X is an antigen targeting peptide. In a specific embodiment, the antigen targeting peptide is a tumor antigen targeting peptide. The tumor antigen can be selected from the group consisting of PSMA, VEGFR, PSCA, EPCam, CD227, EGFR, Alpha-V-beta-3 Integrin, AFP, CD140b, CD30, CD33, CD52, CD56, CD66e, CA125, GD3 ganglioside, CD4, CD20, CD22, CD80, and CD152. In a specific embodiment, the antigen targeting peptide specifically binds an antigen expressed on the surface of cancer cells. In another embodiment, the antigen can be selected from the group consisting of PSMA, VEGFR, PSCA, EPCam, CD227, EGFR, and Alpha-V-beta-3 Integrin.

In yet another embodiment, the antigen targeting peptide specifically binds prostate specific membrane antigen (PSMA). In a further embodiment, X comprises SEQ ID NO:9. The present invention also provides an adenoviral construct comprising a nucleic acid sequence encoding the peptide sequence MAE-X-PDP (SEQ ID NO:45), wherein X is a peptide that specifically binds PSMA. In one embodiment, X comprises SEQ ID NO:9. In another embodiment, an adenoviral construct comprises a nucleic acid sequence encoding the peptide sequence of SEQ ID NO:10.

In the adenoviral constructs of the present invention, the peptide sequence is inserted into the amino acid sequence encoding adenovirus fiber protein. In a specific embodiment, the peptide sequence is inserted into the HI-loop of adenovirus fiber protein. In an alternative embodiment, the peptide sequence is inserted into the EG-loop of adenovirus fiber protein. In another embodiment, the peptide sequence is inserted into the IJ-loop of adenovirus fiber protein.

In additional embodiments, the peptide sequence can be inserted into the C-terminus of capsid protein 1x, the C-terminus of Fiber protein, and the L1-loop of hexon protein. Furthermore, the peptide sequence can be inserted at two or more appropriate sites, e.g., both the HI-loop and C-terminus of Fiber protein.

Furthermore, the adenoviral constructs of the present invention can be modified to ablate interaction with the natural receptor coxsackie and adenovirus receptor (CAR). In specific embodiments, the modification comprises one or more deletions in the nucleic acid sequence encoding adenovirus fiber protein.

In another embodiment, the present invention provides an adenoviral construct comprising a nucleic acid encoding a tumor antigen targeting peptide inserted into the nucleic acid sequence encoding the capsid fiber protein, wherein a nucleic acid sequence encoding the trimer peptide MAE is located upstream of the nucleic acid encoding a tumor antigen targeting peptide and a nucleic acid sequence encoding the trimer peptide PDP is located downstream of the nucleic acid encoding a tumor antigen targeting peptide.

In yet another embodiment, an adenoviral construct comprises a nucleic acid sequence encoding the peptide sequence MAEWQPDTAHHWALTLPDP (SEQ ID NO:9) inserted into the HI-loop of adenovirus fiber protein. The present invention further provides pharmaceutical compositions comprises any of the adenoviral constructs described herein. In another aspect, the present invention relates to the treatment of cancer. In one embodiment, a method for treating cancer comprises administering a therapeutically effective amount of the adenoviral construct of the present invention.

The present invention also provides methods for optimizing adenoviral infection of target cells comprising the steps of (a) generating a peptide-display adenovirus library, wherein the displayed peptide is a peptide that specifically binds an antigen expressed on the surface of a target cell, and wherein the displayed peptide is flanked by random peptide sequences; and (b) screening the peptide-display adenovirus library against the target cells.

In another embodiment, a method comprises (a) generating a peptide-display virus library, wherein the displayed peptide is a peptide that specifically binds an antigen expressed on the surface of a target cell, and wherein the displayed peptide is flanked by random peptide sequences; and (b) screening the peptide-display virus library against the target cells.

In yet another embodiment, the target cell is a cancer cell. In particular embodiments, the virus can be selected from the group consisting of adenovirus, herpes simplex virus, influenza virus, Newcastle disease virus, poliovirus, reovirus, vaccinia virus and vesicular virus. In a specific embodiment, the virus is a retrovirus.

In certain embodiments, one or both of the flanking random peptide sequences are selected from the group consisting of monomer dimer, trimer, tetramer, pentamer, hexamer, septamer, octamer, and a nonamer. In a specific embodiment, the flanking random peptide sequences are multimers. In another embodiment, the flanking random peptide sequences are trimers. In other embodiments, a single peptide sequence at either end of the antigen targeting peptide can be used.

BRIEF DESCRIPTION OF THE FIGURES

FIG. 1 is a schematic illustration of a semi-random Fiber-peptide library.

FIG. 2 lists the library peptide sequences of randomly selected clones from each round.

FIG. 3A-D presents the results of PSMA-mediated adenoviral infection in cell and tumor models. In FIG. 3A, PSMA-targeted infection, LNCaP, PC-3-PSMA (+), and PC-3-PSMA (−) cells were infected with Ad5Track-Luc-Saupw-1 (selected virus) or Ad5Track-Luc-Saurabh (parental virus), MOI=1. Virus infection was quantified by firefly luciferase activity (relative light units, RLU, per mg protein). Columns, averages (n=3). Bars, SE. In FIG. 3B, infection is mediated by PSMA-binding peptide. LNCaP cells were preincubated with serially diluted PSMA-binding peptide or an unrelated control peptide for 30 minutes, followed by infection with Ad5Track-Luc-Saupw-1 or Ad5Track-Luc-WtFiber. Infection was quantified by luciferase activity, relative to non-inhibited infection. Bars represent mean±SE infection of 3 replicates. FIG. 3C, shows the results of adenoviral infection following systemic injection. Mice bearing LNCaP tumors were intravenously injected with Ad5Track-Luc-Saupw-1 or Ad5Track-Luc-WtFiber ($1\times10^9$ IU). After 4 days, viral infection was quantified by ex vivo luciferase activity of tissue lysates. Columns, averages (n=3). Bars, SE. FIG. 3D, shows relative infection results, specifically, tumor to tissue luciferase ratios for each virus 4 days after virus administration. Statistical evaluation: *, P<0.05, , P<0.01, *, P<0.001 (Student's t test).

DETAILED DESCRIPTION OF THE INVENTION

Figure 1B:
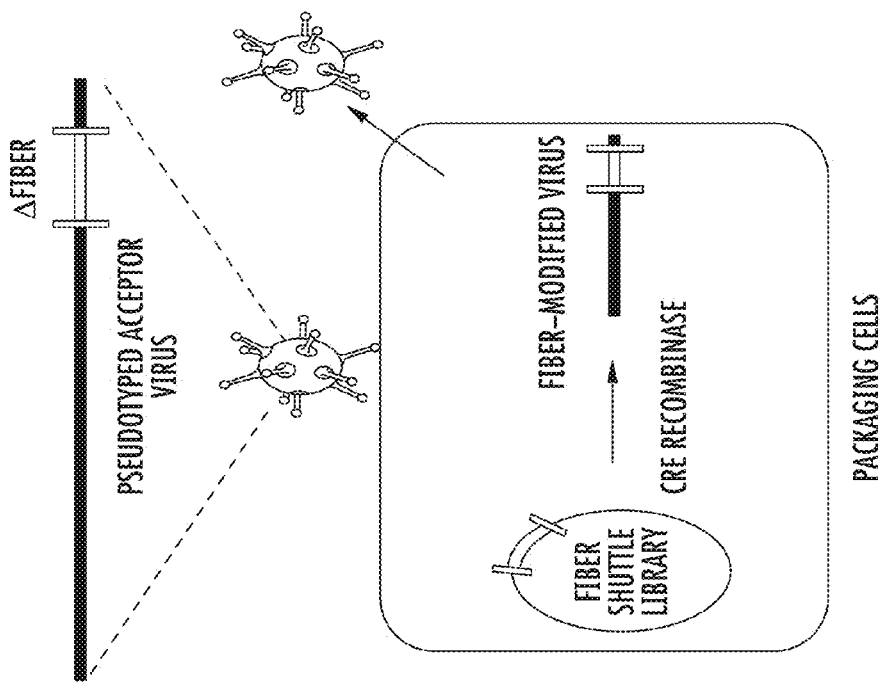
FIG. 1B shows the generation of the adenoviral library. A pseudotyped acceptor virus, lacking any fiber-coding region, was used to infect 293cre57 cells transfected with fiber-shuttle library cassettes. Cre-recombinase site specifically transferred the modified Fiber gene into the infected viral genome, resulting in amplification and packaging of the retargeted virus.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. DEFINITIONS

The term "adenovirus" refers to the virus itself or derivatives thereof. The term covers all serotypes and subtypes and both naturally occurring and recombinant forms, except where otherwise indicated. Thus, the term "adenovirus" or "adenoviral particle" is used to include any and all viruses that can be categorized as an adenovirus, including any adenovirus that infects a human or an animal, including all groups, subgroups, and serotypes. There are at least 51 serotypes of adenovirus that classified into several subgroups. For example, subgroup A includes adenovirus serotypes 12, 18, and 31. Subgroup C includes adenovirus serotypes 1, 2, 5, and 6. Subgroup D includes adenovirus serotype 8, 9, 10, 13, 15, 17, 19, 20, 22-30, 32, 33, 36-39, and 42-49. Subgroup E includes adenovirus serotype 4. Subgroup F includes adenovirus serotypes 40 and 41. These latter two serotypes have a long and a short Fiber protein. Thus, as used herein an "adenovirus" or "adenovirus particle" may include a packaged vector or genome. Depending upon the context, the term "adenovirus" can also include adenoviral vectors.

An "adenovirus vector," "adenoviral vector," or "adenovirus construct" is a term well understood in the art and generally comprises a polynucleotide comprising all or a portion of an adenovirus genome. Thus, an "adenovirus vector," "adenoviral vector," or "adenovirus construct" refers to any of several forms including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a nonviral protein.

In particular embodiments, the adenoviral vector typically contains most of the adenoviral genome. The adenoviral vector may also contain a bacterial origin of replication. In other embodiments, portions of the wild-type adenoviral genome may be deleted to permit insertion of desired products and the packaging of recombinant adenoviral vectors containing the desired genes. In certain embodiments, adenovirus vectors are replication-competent in a target cell. In other embodiments, adenovirus constructs are conditionally replicative in a target cell. Indeed, conditionally replicating adenoviruses (CRAds) represent a promising modality for the treatment of neoplastic diseases, including prostate cancer.

Recombinant adenoviruses are currently used for a variety of purposes, including gene transfer in vitro, vaccination in vivo, and gene therapy. Several features of adenovirus biology have made such viruses the vectors of choice for certain of these applications. For example, adenoviruses transfer genes to a broad spectrum of cell types, and gene transfer is not dependent on active cell division. Additionally, high titers of virus and high levels of transgene expression can generally be obtained.

Decades of study of adenovirus biology have resulted in a detailed picture of the viral life cycle and the functions of the majority of viral proteins. The genome of the most commonly used human adenovirus (serotype 5) consists of a linear, 36 kb, double-stranded DNA molecule. Both strands are transcribed and nearly all transcripts are heavily spliced. Viral transcription units are conventionally referred to as early (E1, E2, E3 and E4) and late, depending on their temporal expression relative to the onset of viral DNA replication. The high density and complexity of the viral transcription units poses problems for recombinant manipulation, which is therefore usually restricted to specific regions, particularly E1, E2A, E3, and E4. In most recombinant vectors, transgenes are introduced in place of E1 or E3, the former supplied exogenously. The E1 deletion renders the viruses defective for replication and incapable of producing infectious viral particles in target cells; the E3 region encodes proteins involved in evading host immunity, and is dispensable for viral production per se.

Two approaches have traditionally been used to generate recombinant adenoviruses. The first involves direct ligation of DNA fragments of the adenoviral genome to restriction endonuclease fragments containing a transgene. The low efficiency of large fragment ligations and the scarcity of unique restriction sites have made this approach technically challenging. The second and more widely used method involves homologous recombination in mammalian cells capable of complementing defective adenoviruses ("packaging lines"). Homologous recombination results in a defective adenovirus which can replicate in the packaging line (e.g., 293 or 911 cells) which supplies the missing gene products (e.g., E1). The desired recombinants are identified by screening individual plaques generated in a lawn of packaging cells. The low efficiency of homologous recombination, the need for repeated rounds of plaque purification, and the long times required for completion of the viral production process have hampered more widespread use of adenoviral vector technology.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "co-administration" refers to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include prostate, breast, colon, lung, brain, kidney, and bladder cancer.

As used herein, the term "cancer cells" refers to individual cells of a cancer. Such cells may include, for example, cells that express prostate specific membrane antigen (PSMA).

The term "polynucleotide" or "nucleic acid" refers to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH$_2$) or a mixed phosphor amidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The term "plasmid" refers to an extrachromosomal circular DNA capable of autonomous replication in a given cell. The range of suitable plasmids is very large. In certain embodiments, the plasmid is designed for amplification in bacteria and for expression in a eukaryotic target cell. Such plasmids can be purchased from a variety of manufacturers. Exemplary plasmids include but are not limited to those derived from pBR322 (Gibco BRL), pUC (Gibco BRL), pBluescript (Stratagene), pREP4, pCEP4 (Invitrogen), pCI (Promega) and p Poly (Lathe et al., Gene 57 (1987), 193-201). Plasmids can also be engineered by standard molecular biology techniques (Sambrook et al., Laboratory Manual, Cold Spring Harbor Laboratory Press, Cold Spring Harbor (1989), N.Y.). It may also comprise a selection gene in order to select or to identify the transfected cells (e.g., by complementation of a cell auxotrophy or by antibiotic resistance), stabilizing elements (e.g., cer sequence) or integrative elements (e.g., LTR viral sequences and transposons).

The term "shuttle plasmid" refers to a plasmid comprising a unique restriction site between certain homologous recombination sites and used to insert a desired nucleic acid molecule, i.e., a. nucleic acid molecule encoding a desired product, into a recombinant adenoviral vector. The homologous recombination sites can be, for example, Ad5 right and Ad5 left. In further embodiments, the shuttle plasmid may have a tissue specific promoter which controls the expression of the desired nucleic acid molecule. The shuttle plasmid also contains a majority of the viral genes necessary to form viral particles. However, the shuttle plasmid does not contain all necessary genes to form viral particles.

The term "promoter" refers to the DNA region, usually upstream of the coding sequence of a gene or operon, which binds RNA polymerase and directs the enzyme to the correct transcriptional start site.

The term "replication" means duplication of a vector. This duplication, in the case of viruses, can occur at the level of nucleic acid, or at the level of infectious viral particle. In the case of DNA viruses, replication at the nucleic acid level comprises DNA replication. In the case of RNA viruses, nucleic acid replication comprises replication into plus or minus strand (or both). In the case of retroviruses, replication at the nucleic acid level includes the production of cDNA as well as the further production of RNA viral genomes. The essential feature is the generation of nucleic acid copies of the original viral vector. However, replication also includes the formation of infectious DNA or RNA viral particles. Such particles may successively infect cells in a given target tissue, thus distributing the vector through all or a significant portion of the target tissue.

The term "sample," as used herein, refers to a biological sample obtained for the purpose of evaluation in vitro. In the methods of the present invention, the sample or patient sample may comprise any body fluid including, but not limited to, blood, serum, plasma, urine, saliva, and synovial fluid. A sample may also comprise any cells, tissue samples or cell components (such as cellular membranes or cellular components) obtained from a patient including a tissue biopsy.

As used herein, the term "subject" refers to any animal (e.g., a mammal), including, but not limited to, humans, non-human primates, rodents, and the like (e.g., which is to be the recipient of a particular treatment). Typically, the terms "subject" and "patient" are used interchangeably, unless indicated otherwise herein.

As used herein, the terms "treatment," "treating," "treat" and the like, refer to obtaining a desired pharmacologic and/or physiologic effect. The terms are also used in the context of the administration of a "therapeutically effective amount" of an agent, e.g., a viral construct of the present invention. The effect may be prophylactic in terms of completely or partially preventing a particular outcome, disease or symptom thereof and/or may be therapeutic in terms of a partial or complete cure for a disease and/or adverse affect attributable to the disease. "Treatment." as used herein, covers any treatment of a disease or condition in a subject, particularly in a human, and includes: (a) preventing the disease or condition from occurring in a subject which may be predisposed to the disease or condition but has not yet been diagnosed as having it; (b) inhibiting the disease or condition, i.e., arresting its development; and (c) relieving the disease or condition, e.g., causing regression of the disease or condition, e.g., to completely or partially remove symptoms of the disease or condition. In particular embodiments, the term is used in the context of treating a subject with cancer.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors," which comprise the attributes of more than one type of vector.

II. GENERATION OF VIRUS-DISPLAYED LIBRARIES

In one aspect, the present invention provides compositions and methods related to the generation or production of virus-displayed, semi-random peptide libraries. In particular embodiments, the viruses are replication competent. In other embodiments, the viruses are conditionally replicative, e.g., the viruses replicate in target cells. Thus, such libraries can be used to optimize infection of the viruses to target cells. In specific embodiments, adenoviruses can be used. Existing adenoviral vectors and systems have been described in U.S. Pat. No. 7,662,795, U.S. Patent Application Publication No. 2005/0245472, U.S. Patent Application Publication No. US 2009/0042257, and U.S. Patent Application Publication No. 2009/0074658, the contents of which are incorporated herein by reference in their entireties. See also, Hogg et al., 18 CANCER GENE THER. 275-87 (2011); Hesse et al., 81(6) J. VIROL. 2688-99 (2007); Majhen et al., 119 VIRUS RES. 121-33 (2006); Waterkemp et al., 8(11) J. GENE MED. 1307-19 (2006); McVey et al., 84 J. GEN. VIROL. 3417-22 (2003). See generally, Young et al., 208 J. PATHOL. 299-318 (2006); Lupold and Rodriguez, 3 CANCER THER. 267-84 (2005); and Lin et al., 11 CANCER GENE THER. 643-64 (2004).

In the context of adenovirus, the capsid shell comprises three major coat proteins—hexon, penton and fiber—and several small proteins that aid in assembly and maintenance of capsid structure. The nucleic acids encoding targeting peptide and random peptide sequence (single or flanking) can be inserted into a part of the nucleic acid sequence that encodes the capsid shell. The nucleic acids can be inserted into one or more of the late genes (L1-L5). In particular embodiments, the nucleic acids are inserted into the sequence that encodes the fiber protein. More particularly, the nucleic acid sequences are inserted into the sequence that encodes the fiber shaft. Alternatively, insertion can take place in the region that encodes the knob domain. In other embodiments, the nucleic acid sequence encoding the flanking peptide sequence and the antigen targeting peptide can be inserted in the HI loop of the fiber protein. In a further embodiment, the nucleic acid sequence encoding the flanking peptide sequence and the antigen targeting peptide can be inserted in the EG loop of the fiber protein. In yet another embodiment, the nucleic acid sequence encoding the flanking peptide sequence and the antigen targeting peptide can be inserted in the IJ loop of the fiber protein. The flanking peptide sequence and the antigen targeting peptide can also be inserted into the C-terminus of capsid protein 1x, the C-terminus of Fiber protein, and the L1-loop of hexon protein. Through routine experimentation, a suitable insertion point in the viral genome can be determined based on the size and sequence of the peptide cassette and antigen targeting peptide. Furthermore, the peptide cassette and antigen targeting peptide can be inserted at the same time in two or perhaps more sites, e.g., both the HI-loop and C-terminus of Fiber protein.

The present invention, however, is not limited to adenoviruses, as any viruses capable of being used to generate a library (e.g., replication competent or conditionally replicative) as described herein can be used including, but not limited to, herpes simplex virus (Keil et al., 143(1) VET. MICROBIOL. 29-36 (2010); Spear at el., 107(1) J. VIROL. METHODS 71-9 (2003)), retroviruses (Nikles et al., 79(7) J. VIROL. 4033-42 (2005); Buckholz et al., 16(1) NAT. BIOTECHNOL. 951-54 (1998)), influenza virus, baculovirus (Grabherr et al., 10(3) CURR. GENE THER. 195-200 (2010); Kitidee et al., 10 BMC BIOTECH. 80-101 (2010); Oker-Blom et al., 2(3) BRIEFINGS IN FUNCTIONAL GENOMICS AND PROTEOMICS 244-53 (2003)), Newcastle disease virus, poliovirus, reovirus, vaccinia virus and vesicular virus.

III. RANDOM AMINO ACID CASSETTES

As described herein, the compositions and methods of the present invention relate to the use of peptide cassettes to flank an antigen targeting peptide that is displayed on the virus. Using the disclosure provided herein and the knowledge of one of ordinary skill in the art, a library of virus-displayed antigen targeting peptides with random, flanking peptide sequences can be generated and screened for those peptide sequences that improve and/or optimize the targeting infection of the virus. The random peptide sequences provide an optimal environment for peptide display and encourage native folding of the viral capsid proteins.

In particular embodiments, peptide sequences that flank the antigen targeting peptides are used. In other embodiments, a single peptide sequence at either end of the antigen targeting peptide can be used. Indeed, although the description discusses the use of "flanking" peptide sequences, it is understood that the present invention applies to the use of peptide sequences on one or both ends of the antigen targeting peptide.

In the generation of the virus-displayed library, randomly generated peptide cassette(s) are used. Based on the results of initial screening, particular substitutional variants can be generated and tested. For example, amino acids may be substituted based on side-chain properties. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Conservative substitutions involve exchanging of amino acids within the same class.

In one embodiment, the random peptide cassettes are monomers. The monomer peptides can be the same or different. In another embodiment, the random peptide sequences that flank the antigen targeting peptide are multimers. Similarly, the flanking multimers can be the same or different sequences, and/or the same or different length of amino acids. In particular embodiments, the flanking monomers can be any one of a combination of a monomer, a dimer, a trimer, a tetramer, a pentamer, a hexamer, a septamer, an octamer, a nonamer, and the like.

IV. PEPTIDES FOR TARGETING THE PROSTATE SPECIFIC MEMBRANE ANTIGEN (PSMA)

In particular embodiments, the antigen targeting peptide is PSMA. PSMA is a type II transmembrane protein found predominantly in the prostate, with minor expression of isoforms in the small intestine, brain, and tumor neovascularity. (Heston. 35 UROLOGE A. 400-07 (1996)). Though the precise function of PSMA is not known, it is known to be a membrane bound carboxypeptidase and folate hydrolase. Id. This protein can exist in two forms, PSMA and PSM'. PSMA is the membrane bound form and PSM' is an intracellular form which lacks the transmembrane domain at the amino terminus. PSM' is the predominant form in the benign prostatic cell, while PSMA expression increases and predominates with the more aggressive prostate cancer tumor grades. From a clinical point of view, PSMA has all the features necessary for consideration as a systemic target for metastatic prostate cancer. Namely, its expression increases in aggressive cancers, androgen suppression results in up regulation, and background expression in other tissues does not appear to be a clinically significant source of aberrant targeting. See, e.g. Gong, et al., 4 MOL. UROL. 217-23 (2000)).

The methods and compositions of the present invention can be used in conjunction with peptides targeting PSMA. Examples of peptides that specifically target PSMA include, but are not limited to, U.S. Pat. No. 7,749,968, U.S. Pat. No. 7,666,425, U.S. Pat. No. 7,476,513, U.S. Pat. No. 7,381,407, U.S. Pat. No. 7,163,680, and U.S. Pat. No. 7,112,412. See also, U.S. Patent Application Publication No. 2009/0274625, U.S. Patent Application Publication No. 2009/0238755, U.S. Patent Application Publication No. 2009/0041789, U.S. Patent Application Publication No. 2007/0254316, U.S. Patent Application Publication No. 2007/0128671, U.S. Patent Application Publication No. 20060275212, U.S. Patent Application Publication No. 2004/0024188, and U.S. Patent Application Publication No. 2003/0031673.

V. OTHER ANTIGENS/TARGET CELLS

The present invention also relates to the use of other antigens implicated in cancer. The compositions and methods of the present invention can be used to generate viruses that display other tumor antigens flanked by peptide sequences that improve infection of target cancer cells. The type of cancer can include, but is not limited to, carcinoma, lymphoma, blastoma, sarcoma, and leukemia or lymphoid malignancies. More particular examples of such cancers include small intestine cancer, bladder cancer, lung cancer, thyroid cancer, uterine cancer, liver cancer, kidney cancer, breast cancer, stomach cancer, testicular cancer, cervical cancer, esophageal cancer, ovarian cancer, colon cancer, melanoma, prostate cancer, and the like.

Any known cancer/tumor antigen can be used in the context of the present invention. The antigen can be, but is not limited to, MAGE, MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its antigenic epitopes CAP-1 and CAP-2, etv6, amII, Prostate Specific Antigen (PSA) and its antigenic epitopes PSA-1. PSA-2, and PSA-3. T-cell receptor/CD3-Z chain, MAGE-family of tumor antigens (e.g., MAGE-A1, MAGE-A2. MAGE-A3. MAGEA4, MAGE-A5. MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGEC5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21 ras, RCAS1, α-fetoprotein, E-cadherin, α-catenin, 13-catenin, γ-catenin, p12Octn, gp100Pmel117, FRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, HA, EBV-encoded nuclear antigen (EBNA)-1, brain glycogen phosphorylase, SSX-1, SSX-2 (HOM-MEL40), SSX-3, SSX-4, SSX-5, SCP-1 and CT-7, and c-erbB-2, acute lymphoblastic leukemia (etv6, amII, cyclophilin b), B cell lymphoma (Ig-idiotype), glioma (E-cadherin, a-catenin, 13-catenin, 7-catenin, p12Octn), bladder cancer (p21 ras), biliary cancer (p21 ras), breast cancer (MUC family, HER2/neu, c-erbB-2), cervical carcinoma (p53, p21 ras), colon carcinoma (p21 ras, HER2/neu, c-erbB-2, MUC family), colorectal cancer (Colorectal associated antigen (CRC)-0017-1A/GA733, APC), choriocarcinoma (CEA), epithelial cell cancer (cyclophilin b), gastric cancer (HER2/neu, c-erbB-2, ga733 glycoprotein), hepatocellular cancer, Hodgkins lymphoma (lmp-1, EBNA-1), lung cancer (CEA, MAGE-3, NY-ESO-1), lymphoid cell-derived leukemia (cyclophilin b), melanoma (p15 protein, gp75, oncofetal antigen, GM2 and GD2 gangliosides, MelanA/MART-1, cdc27, MAGE-3, p21ras, gp100.sup.Pmel117), myeloma (MUC family, p21ras), non-small cell lung carcinoma (HER2/neu, c-erbB-2), nasopharyngeal cancer (lmp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ES0-1), and T cell leukemia (HTLV-1 epitopes).

In particular embodiment, the tumor antigen can be selected from the group consisting of PSMA, VEGFR, PSCA, EPCam, CD227, EGFR, Alpha-V-beta-3 Integrin, AFP, CD140b, CD30, CD33. CD52, CD56, CD66e, CA125, GD3 ganglioside, CD4, CD20, CD22, CD80, and CD152. In a specific embodiment, the antigen targeting peptide specifically binds an antigen expressed on the surface of cancer cells. In another embodiment, the antigen can be selected from the group consisting of PSMA. VEGFR, PSCA, EPCam, CD227, EGFR, and Alpha-V-beta-3 Integrin.

The present invention can also be used with other antigen targeting peptides to optimize targeting infection of target cells. Target cells can include, but are not limited to, bacterial cells, fungal cells, diseased cells, or generally any foreign cells. Indeed, the present invention can be used to target viral infection using an antigen targeting peptide specific for the target cell of choice.

VI. PHARMACEUTICAL COMPOSITIONS/DELIVERY OF VIRAL CONSTRUCTS

Accordingly, a pharmaceutical composition of the present invention may comprise an effective amount of at least one viral construct. In a specific embodiment, an effective amount of a recombinant adenoviral vector comprising a nucleic acid sequence encoding the peptide sequence MAEWQPDTAHHWALTLPDP (SEQ ID NO:10) inserted into the HI-loop of adenovirus fiber protein can be administered to a subject or patient suffering from prostate cancer. Although the following description of pharmaceutical compositions and disease assessment is described in the context of prostate cancer, it is understood that the disclosure is not so limiting and that the present invention is applicable to other types of cancer as well as other disease platforms depending on the antigen targeting peptide used.

As used herein, the term "effective" means adequate to accomplish a desired, expected, or intended result. More particularly, the terms "effective amount" and "therapeutically effective amount" are used interchangeably and refer to an amount of at least one viral construct, perhaps in further combination with another therapeutic agent, necessary to provide the desired treatment or therapeutic effect, e.g., an amount that is effective to prevent, alleviate, treat or ameliorate symptoms of a disease or prolong the survival of the subject being treated. In particular embodiments, the pharmaceutical compositions of the present invention are administered in a therapeutically effective amount to treat a subject suffering from cancer. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The pharmaceutical compositions of the present invention are in biologically compatible forms suitable for administration in vivo to subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the at least one viral construct is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of at least one viral construct together with a suitable amount of a pharmaceutically acceptable carrier so as to provide the form for proper administration to the patient. In particular embodiments that comprise the administration of a viral construct and another therapeutic agent, the therapies can be separately formulated and administered according to the present invention. The formulation should suit the mode of administration.

Delivery of the viral constructs of the present invention (e.g., adenoviral) can be accomplished by either site-specific injection (local administration) or intravenously (systemic administration). Site-specific injections of adenoviral vectors may include, for example, injections into the portal vein of the liver as well as intraperitoneal, intrapleural, intrathecal, intra-arterial, intra-tumor injections or topical application. These methods are easily accommodated in treatments using adenoviral vectors.

Furthermore, the pharmaceutical compositions of the present invention may be administered by any other particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means.

The adenoviral vectors may be delivered to the target cell in a variety of ways, including, but not limited to, liposomes, general transfection methods that are well known in the art (such as calcium phosphate precipitation or electroporation), direct injection, and intravenous infusion. The means of delivery will depend in large part on the particular adenoviral vector (including its form) as well as the type and location of the target cells (i.e., whether the cells are to be transfected or transformed in vitro or in vivo). If used as a packaged adenovirus, adenovirus vectors may be administered in an appropriate physiologically acceptable carrier at a dose of about 1 to about 10 µg. The multiplicity of infection will generally be in the range of about 0.001 to 100. If administered as a polynucleotide construct (i.e., not packaged as a virus) about 0.01 µg to about 1000 µg of an adenoviral vector can be administered. The adenoviral vector/construct may be administered one or more times, depending upon the intended use and the immune response potential of the host, and may also be administered as multiple, simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

Thus, the adenoviral vector/construct, the polynucleotide and expression vector or the viral particle of the present invention may be delivered in vivo to the human or animal organism by specific delivery means adapted to the pathology to be treated. For example, a balloon catheter or a stent coated with the adenoviral vector/construct, the expression vector carrying the polynucleotide or the viral particle may be employed to efficiently reach the cardiovascular system. It is also possible to deliver the therapeutic agents by direct administration, e.g., intravenously, in an accessible tumor, in the lungs by aerosolization, and the like.

Alternatively, one may employ eukaryotic host cells that have been engineered ex vivo to contain the adenoviral vector, the expression vector carrying the polynucleotide or the viral particle according to the invention. Methods for introducing such elements into a eukaryotic cell are well known to those skilled in the art and include microinjection of minute amounts of DNA into the nucleus of a cell, transfection with calcium phosphate, electroporation, lipofection/liposome fusion, and particle bombardment.

Administration of the above-described methods may also include repeat doses or courses of target-cell specific adenovirus depending, inter alia, upon the individual's response and the characteristics of the individual's disease. Repeat doses may be undertaken immediately following the first course of treatment (i.e., within one day), or after an interval of days, weeks or months to achieve and/or maintain suppression of tumor growth.

Generally, an effective amount of an adenovirus vector is administered, i.e., amounts sufficient to achieve the desired result, based on general empirical knowledge of a population's response to such amounts. Some individuals are refractory to these treatments, and it is understood that the methods encompass administration to these individuals. The amount to be given depends, inter alia, on the stage of the cancer, the condition of the individual, the extent of disease, the route of administration, how many doses will be administered, and the desired objective.

The methods of the present invention can be applied to the treatment of prostate cancer in male subjects at any stage of the cancer, although certain treatment methods are more preferred for particular cancer stages. Prostate cancer is commonly evaluated according to a scale divided into four lettered stages: A, B, C and D. Tumors in stage A are microscopic; stage A1 designates tumors confined to a relatively small area and composed of well-differentiated tissue, while stage A2 tumors are more diffuse and less well differentiated. Stage B tumors are large enough to be felt during a rectal examination, while stage C prostate cancers have spread throughout the gland and typically have pushed past the borders of the prostate into surrounding structures. Stage D tumors have metastasized, e.g., to lymph nodes, bone, or other organs. Alternatively, tumors can be staged by the TNM staging system, in which tumors are ranked on a scale of progressively worsening disease from T1a to T4b (e.g., Tic tumors are non-palpable and non-visible that were detected by elevated blood levels of prostate specific antigen). The methods of the present invention are useful in the treatment of any stage of prostate cancer. However, it will be appreciated by the skilled artisan that methods involving procedures for removal or destruction of prostatic tumor tissue preferably are employed with non-metastasized cancers. For example, radical prostatectomy can be used with stage A, B and some stage C tumors (i.e., where the tumor growth has not extended considerably beyond the borders of the prostate gland) as well as stage Tic tumors. Radiation therapy (e.g., external or interstitial) preferably is used with stage A, B or C tumors as well as Tic tumors.

To assess the efficacy of a treatment method of the invention, the size of the prostate can be determined by methods known in the art, for example, rectal examination, transrectal ultrasonography or magnetic resonance imaging (MRI). Moreover, the size or extent of the prostate tumor (and metastatic tumors, if any) can be assessed by known methods including a prostate-specific antigen blood test, bone scanning, X-rays, skeletal survey, intravenous pyelography, CAT-scan, MRI, physical examination, biopsy, and the like. For treatment methods that involve surgery (e.g., in neoadjuvant therapy wherein a peptide compound is administered prior to a radical prostatectomy), the tumor can also be staged during surgery (e.g., the prostate gland can be examined during surgery and/or a biopsy can be taken and examined). Thus, clinical staging and/or surgical staging may be used to evaluate the extent of disease.

One method of evaluating the extent of prostate cancer is to assay the level of prostate-specific antigen (PSA) in a subject's blood. The PSA blood test is a reasonably specific, sensitive, rapid, and inexpensive tool for screening for prostate cancer. In general, a blood PSA level above 4 ng/ml is considered to be suggestive of the presence of prostate cancer, with levels above 10 ng/ml being particularly indicative of cancer. For a subject undergoing treatment with a viral construct according to the methods of the invention, a pretreatment level of PSA can be established and the efficacy of the treatment assessed by monitoring periodically the PSA level in the subject's blood, wherein decreased PSA levels are used as an indicator of the efficacy of the treatment. The PSA nadir (i.e., the point at which PSA levels do not decrease further even upon further treatment with a viral construct) can be used as the indicator point for initiation of a second therapy, for example fin performance of a procedure that removes or destroys prostatic tumor tissue (including radical prostatectomy, cryosurgery and or radiation therapy). It is expected that the PSA nadir will be reached sooner using a viral construct, as compared to treatments which do not include using a viral construct of the present invention.

Additionally or alternatively, plasma concentrations of sex hormones can be monitored to assess the efficacy of the drug therapy. Concentrations of hormones such as testosterone, dihydrotestosterone, dehydroepiandrosterone (DHEA), DHEA-sulfate, androst-5-ene-3β, 17-diol, and the estrogen 17β-estradiol can all be measured by methods known to the skilled artisan. Preferably, decreased levels of testosterone and dihydrotestosterone can be used as indicators of treatment efficacy.

In another embodiment, the compositions and methods of the invention can be administered in conjunction with other known treatments for cancer including, but not limited to, mechanical removal of cancerous cells (e.g., surgical removal of a tumor), and administration of chemotherapeutic agents. There are many known chemotherapeutic agents used to treat cancer which act to kill cancer cells and/or slow their growth through other mechanisms. The administrations of such additional treatments and/or agents are intended to be included in the methods of the present invention.

For example, examples of chemotherapeutic agents that may be used in conjunction with the compositions and methods of the present invention include, but are not limited to, antimetabolites such as folate analogs (e.g., methotrexate), purine analogs (e.g., fludarabine, mercaptopurine, and thioguanine (e.g., 6-TG)), adenosine analogs (e.g., cladribine, and pentostatin), pyrimidine analogs (e.g., capecitabine, cytarabine, depocyt, floxuridine, fluorouracil (e.g., 5-FU); and gemcitabine), and substituted ureas (e.g., hydroxyurea); natural products such as antitumor antibiotics (e.g., bleomycin, dactinomycin, actinomycin D, daunorubicin, daunomycin, DaunoXome (liposomal daunorubicin), doxorubicin, Doxil (liposomal-doxorubicin), epirubicin, idarubicin, mitoxantrone, and mitomycin C), epipodophyllotoxins (e.g., etoposide and teniposide), microtuble agents (e.g., docetaxel, paclitaxel, vinblastine, vincristine, and vinorelbine), camptothecin analogs (e.g., irinotecan and topotecan), enzymes (e.g., asparaginase), and monoclonal antibodies (e.g., alemtuzamab, gemtuzumab ozogamicin, ibritumomab tiuxetan, nofetumomab, rituximab, tositumomab, and trastuzumab). Those skilled in the art will recognize that any of these chemotherapeutic agents and others can be used in combination with the viral constructs of the present invention.

One aspect of the invention relates to a method for treating prostate cancer in a subject in need of such treatment, comprising administering to the subject a viral construct/particle (e.g., adenoviral) of the present invention, and performing on the subject at least one procedure that removes or destroys prostatic tumor tissue, such as a radical prostatectomy, cryosurgery, external radiation therapy (e.g., X-ray therapy) or interstitial radiation therapy (e.g., implantation of a radioactive seed). The adenoviral construct may be administered to the subject prior to or subsequent to performing the procedure that removes or destroys pro static tumor tissue. In one such embodiment, administration of an viral construct is preferably for a period sufficient to cause the prostate or prostatic tumor tissue to shrink in size prior to performing the procedure that removes or destroys prostatic tumor tissue. A suitable period for preadministration of a viral construct typically is between about one day and about one year, more preferably between about three days and about six months.

In certain situations, it may be desirable to use an antiandrogen, and thus in another embodiment, this treatment method can further involve administering an antiandrogen to the subject in combination with the viral construct. In yet another embodiment, this treatment method can further involve administering one or more inhibitors of sex steroid biosynthesis to the subject in combination with the viral construct (optionally in further combination with an antiandrogen) prior to or subsequent to performing the procedure that removes or destroys prostatic tumor tissue.

In another embodiment, the viral construct of the present invention may be administered in conjunction with an LHRH agonist, as described in U.S. Pat. No. 5,843,902, U.S. Pat. No. 5,780,435, and U.S. Pat. No. 6,153,586, the contents of which are incorporated herein by reference in their entireties, or an LH receptor antagonist.

Those of skill in the art will recognize that while it may not be necessary to combine viral construct therapy with additional drugs or treatments, in certain situation it may be desirable to further combine the viral construct with other drugs or treatments to achieve the greatest therapeutic effect.

In another aspect, the viral constructs and therapeutic agents of the present invention may be combined with other agents including, but not limited to, immunomodulatory agents, anti-inflammatory agents (e.g., adrenocorticoids, corticosteroids beclomethasone, budesonide, flunisolide, fluticasone, triamcinolone, methlyprednisolone, prednisolone, prednisone, hydrocortisone), glucocorticoids, steroids, non-steriodal anti-inflammatory drugs (e.g., aspirin, ibuprofen, diclofenac, and COX-2 inhibitors), and leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents, and antibiotics (e.g., dactinomycin (formerly actinomycin), bleomycin, erythomycin, penicillin, mithramycin, and anthramycin (AMC)).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described processes. Only reasonable and routine experimentation will be required to optimize such process conditions.

Materials and Methods

Cell Lines.

293cre57 cells were provided by Stephen Langer (University of Colorado). Cre-recombinase activity was authenticated by Cre Stop light assay. PC-3-PSMA cells were provided by Warren Heston (Cleveland Clinic) and authenticated for PSMA expression by Western blot and ELISA. DPL-S11 cells are generated as described. See Hoti et al., 17 CANCER GENE THER. 1-13 (2010). PC-3, 293, and LNCaP cells were obtained from ATCC and were not further authenticated.

Fiber-Shuttle Vector.

Generation of fiber-shuttle plasmid for the Coxsackie and Adenovirus Receptor (CAR) binding ablation by deletion of amino acids $T_{489}AYT_{492}$ (SEQ ID NO:46) in the FG loop has been described previously. See Lupold et al., 35 NUCLEIC ACIDS RES. e138 (2007); and Roelvink et al., 286 SCIENCE 1568-71 (1999). An additional site mutation ($Y_{477}A$) was performed using site directed mutagenesis kit (Invitrogen, Carlsbad, Calif.) with primers BFB-1: CTTCCTGGAC-CCAGAAGCTTGGAACTTTAGAAATG (SEQ ID NO:1) and BFB-2 CATTTCTAAAGTTCCAAGC-TTCTGGGTC-CAGGAAG (SEQ ID NO:2), where the underlined sequences represent the desired mutation. See Shayakhmetov et al., 79 J. VIROL. 7478-91 (2005); and Alemany et al., 8 GENE THER. 1347-53 (2001). An SspI restriction enzyme recognition site was ablated by this mutation and thus serves as a means to identify the new desired vector prior to sequencing. The entire Fiber coding region of the resulting shuttle plasmid was sequenced with primers M13 forward (5'-GTAAAACGACGGCCAGT) (SEQ ID NO:3), M13 reverse (5'-GGAAACAGCTATGACCATG) (SEQ ID NO:4), Fiber-S2 (5'-CTCACCCCCTCTAACTACTG) (SEQ ID NO:5) and Fiber-S3 (5'-CAGGAGATGGGCTT-GAATTT) (SEQ ID NO:6), and the integrity was confirmed. The resulting fiber-shuttle plasmid, RPuc-FBR-8, received the insertion of retargeting peptide cassettes through EcoRI/BspEI subcloning.

Library Insert.

Oligonucleotides encoding PSMA-binding peptide (WQPDTAHHWATL) (SEQ ID NO:9) (Aggarwal et al., 66 CANCER RES. 9171-77 (2006)), flanked by three random amino acid coding cassettes were generated at library scale and quality. The oligonucleotide library template, 5'-Biotin-TGGAGTTGTGTCTCCGGAMNNMNNMNNC AGTGT-TGCCCAGTGGTGTGCGGTATCAGGCTGCCAMNN-MNNMNNGAATTCGGATTC CTGTGTACCGCT (SEQ ID NO:7) is the reverse complement of the coding region, where N refers to all possible nucleotides (A, G, C, & T) and M refers to only C or A. The extension primer Lib001 (5'-Biotin-AGCGGTACAGGAATCC) (SEQ ID NO:8) was applied to create double-stranded DNA product. The template was annealed with the extension primer and extended with klenow fragment DNA polymerase (New England Biolabs, Beverly, Mass.). The products were then restriction digested with BspEI and EcoRI. The unwanted digested ends were purified away by streptavidin magnetic beads (New England Biolabs). Double-stranded DNA insert was ligated into the HI-loop of CAR-binding ablated fiber-shuttle plasmid in large scale to maintain library diversity. Completed ligation was electroporated into electrocompetent DH5α and grown in SOC broth at 37° C. for 30 minutes. Prior to amplification, serial dilutions were plated on LB agar with selective antibiotic, and the diversity of this shuttle plasmid library was estimated at 2×10$^6$ clones. Sequencing of random clones demonstrated library integrity and diversity. The combined cultures were grown in large scale for purification of the fiber-peptide-shuttle library.

Construction of the Adenovirus-Displayed Peptide Library.

Figure 1A:
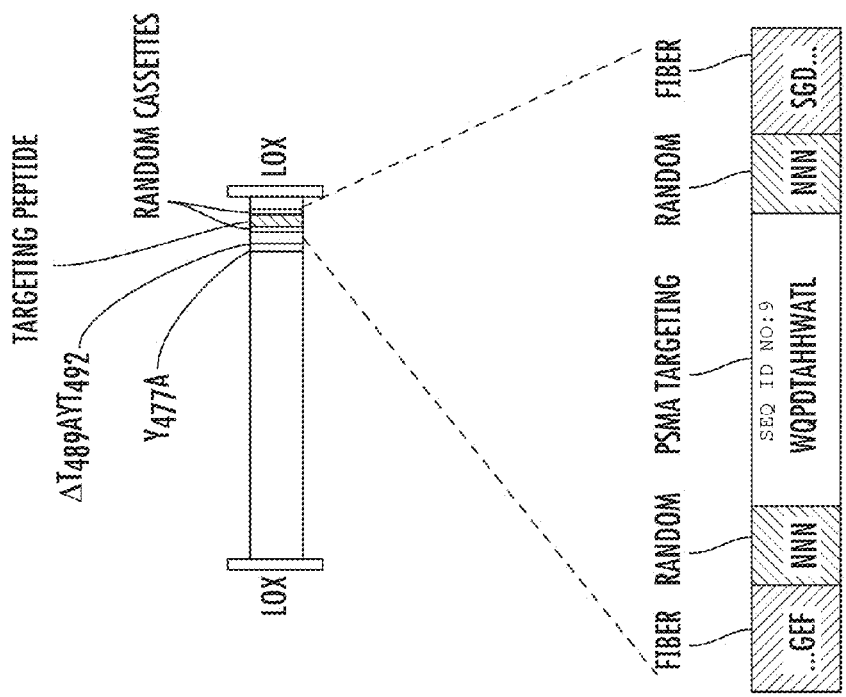
In FIG. 1A, the Fiber library, a pre-selected PSMA-targeting peptide, WQPDTAHHWATL (SEQ ID NO:9), was cloned into the HI-loop of fiber knob and flanked by 2 random trimer peptide cassettes providing a potential diversity of 64 million different peptide orientations. The Fiber gene was further modified by $\Delta T_{489}AYT_{492}$ (SEQ ID NO:46) and $Y_{477}A$ to ablate interaction with the natural receptor, CAR. The entire Fiber gene region is flanked by noncompatible unidirectional lox sites (green rectangle) for site-directed cassette exchange.

Oligonucleotides encoding PSMA-binding peptide (Aggarwal et al., 66 CANCER RES. 9171-77 (2006)), flanked by 3 random amino acid cassettes, were synthesized and subcloned into the HI-loop of CAR-ablated Fiber in RPuc-FBR8 ($\Delta T_{489} AYT_{492}$, $Y_{477}A$ (SEQ ID NO:46); FIG. 1A) at library scale. The resulting Fiber-peptide shuttle library was recombined into the Fiber region of pseudotyped adenovirus serotype 5 (Ad5), Ad5Track-Luc-Fex or Ad5-PSE-PBN-E1A-Fex [multiplicity of infection (MOI)=1], by Cre-recombinase-mediated cassette exchange in 6×10$^6$ 293cre57 cells and purified at 72 hours as previously described. See FIG. 1B and Lupold et al., 35 NUCLEIC ACIDS RES. E138 (2007).

In Vitro Library Screening.

Target cells were infected (MOI=1) for 2 hours (round 1) or 1 hour (subsequent rounds), washed, and incubated for 3 to 4 days. Counterselections were conducted for 1 hour in rounds 2 to 3 prior to positive selection (Table 1 below). The floxed Fiber-coding region was PCR rescued into the RPuc-Rescue shuttle vector (Lupold et al., 35 NUCLEIC ACIDS RES. E138 (2007)), and 10 to 30 individual clones for each round were sequenced. The remaining library was amplified on a large scale and applied as the shuttle vector for the next round.

TABLE 1

Screening of Adenovirus-Displayed Peptide Library in a PSMA-Expressing Cancer Cell and Tumor Model

| | SCREENING ROUND | | | |
|---|---|---|---|---|
| | I | II | III | IV |
| Screening Type | In vitro | In vitro | In vitro | In vivo |
| E1 gene Cassette | GFP | GFP | GFP | PSE-PBN-E1A |
| Counter Selection | N/A | 293 | PC-3 | Systemic injection |
| Positive Selection | 293-PSMA | LNCaP | LNCaP | LNCaP tumor |

In Vivo Selection.

Subcutaneous LNCaP tumors in male athymic nu/nu mice (Charles River Laboratories) were grown to ~0.5 cm$^3$ in dimension, and 10$^6$ infectious units (IU) of Ad5-PSE-PBN-PSMA library was injected via tail vein. After 3 weeks, the tumor, kidney, lung, spleen, and liver were collected, total DNA were extracted, and the Fiber region was PCR amplified and subcloned as described earlier. Thirty clones were randomly sequenced.

Luciferase Assays.

Cells were infected (MOI=1) in 96-multiwell plates for 1 hour, washed, fed complete media, and assayed for luciferase activity at 48 hours (Promega). Competition studies applied serially diluted peptide 30 minutes prior to infection.

Bioluminescence Imaging.

LNCaP tumor-bearing mice were anesthetized with isoflurane 3 days after viral infection and D-luciferin was injected intraperitoneally. Bioluminescence images were observed with an in vivo imaging system (IVIS; Xenogen) and analyzed using Live Image software (Xenogen).

Virus Purification.

Recombinant adenovirus was purified by commercial adenovirus purification kit (Adenopure; Puresyn) or iodixanol discontinuous density gradient ultracentrifugation and size exclusion column chromatography. Peng et al., 354 ANAL. BIOCHEM. 140-47 (2006). Virus titer was determined by Adeno-XTM Rapid Titer Kit (BD Biosciences) or GFP using DPL-S11 cells expressing an artificial anti-Fiber single-chain antibody receptor. See Hoti et al., 17 CANCER GENE THER. 1-13 (2010).

Example 1

Generating an Adenovirus-Displayed, Semi-Random Peptide Library

To generate an adenovirus-displayed, semirandom peptide library, a phage-derived PSMA-targeting peptide, WQPDTAHHWATL (SEQ ID NO: 9) (Aggarwal et al., 66 CANCER RES. 9171-77 (2006)), flanked by 3 random amino acid cassettes, was first subcloned into the HI-loop of an Ad5 Fiber-shuttle vector (FIG. 1A). The host Fiber gene was detargeted from CAR-mediated infection through FG-loop $T_{489}AYT_{492}$ (SEQ ID NO:46) deletion and DE-loop $Y_{477}A$ mutation. Roelvink et al., 286 SCIENCE 1568-71 (1999). The Fiber region of the shuttle library was unidirectionally transferred into the native Ad5 Fiber region by Cre-recombinase-mediated cassette exchange in 6×10$^6$ packaging cells (FIG. 1B). Previous studies indicate that a library diversity of at least 10$^5$ can be achieved by this method. See Lupold et al., 35 NUCLEIC ACIDS RES. e138 (2007). The resulting adenovirus library was harvested within a single life cycle to prevent the generation of hybrid capsids, which could occur after virus spread and coinfection. This adenovirus library approach can produce a high complexity of potential conformations for Fiber protein folding, peptide folding, and orientation for peptide-target interaction.

The resulting adenovirus library was biopanned against PSMA-positive cell lines and tumors to isolate those adenoviruses that preferentially utilize PSMA as an alternative receptor (Table 1). Specifically, the initial adenovirus library was incubated with PSMA-expressing cells for 1 hour at a density of 1 IU per cell; the cells were then washed and incubated for 3 days. Fiber gene cassettes from successfully infectious round 1 virus were rescued by PCR amplification and subcloning, via Cre-recombinase-mediated cassette exchange, to generate a second-round Fiber-shuttle library and finally a second-round adenovirus-displayed peptide library. Various cell lines were used for counter- and positive-selections to minimize amplification of virus that infected via PSMA-independent mechanisms. Ten to 20 Fiber-shuttle clones from each selection round were sequenced both to ensure diversity and to identify potential candidates. By the third round, 6 unrelated candidate peptides were represented by multiple clones, indicating library maturation (FIG. 2).

To identify the most successful targeted virus, the fourth-round library was generated as a conditionally replicating virus library (Ad5-PSE-PBN-E1A-PSMA-Lib), which utilizes an androgen receptor-responsive cassette to drive EIA gene expression and viral replication. This replication-competent library was applied to a final and stringent in vivo selection, by intravenous injection, and allowed 3 weeks for viral infection, amplification, and spread within the LNCaP tumor. The tumor was harvested, and peptide cassettes from the infectious viruses were rescued by PCR amplification and Cre-recombinase subcloning. Thirty randomly picked clones were sequenced and, surprisingly, a single peptide sequence (MetAEWQPDTAHHWATLPDP, named Saupw-1) (SEQ ID NO:10) was identified in all 30 clones. Diversity of the input fourth-round library was reconfirmed by sequencing, suggesting that the in vivo selection was extremely stringent and resulted in a single, successful targeting peptide.

Example 2

Evaluation of Adenovirus Constructs

Figure 3A:
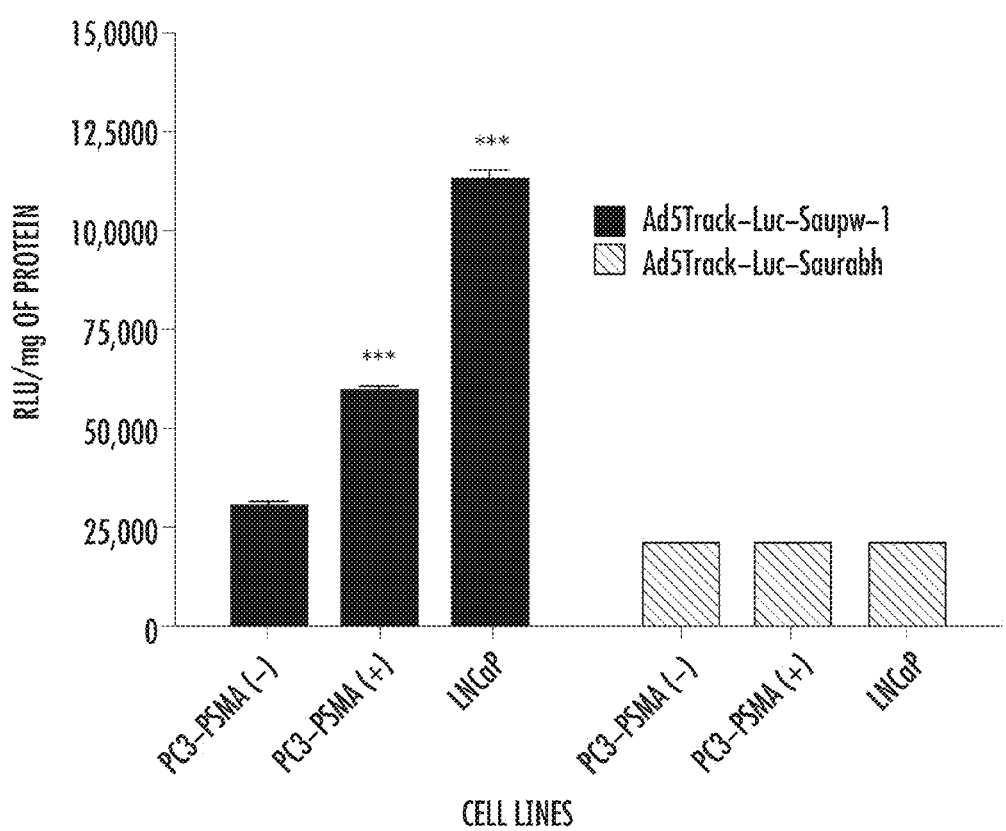
Figure 3B:
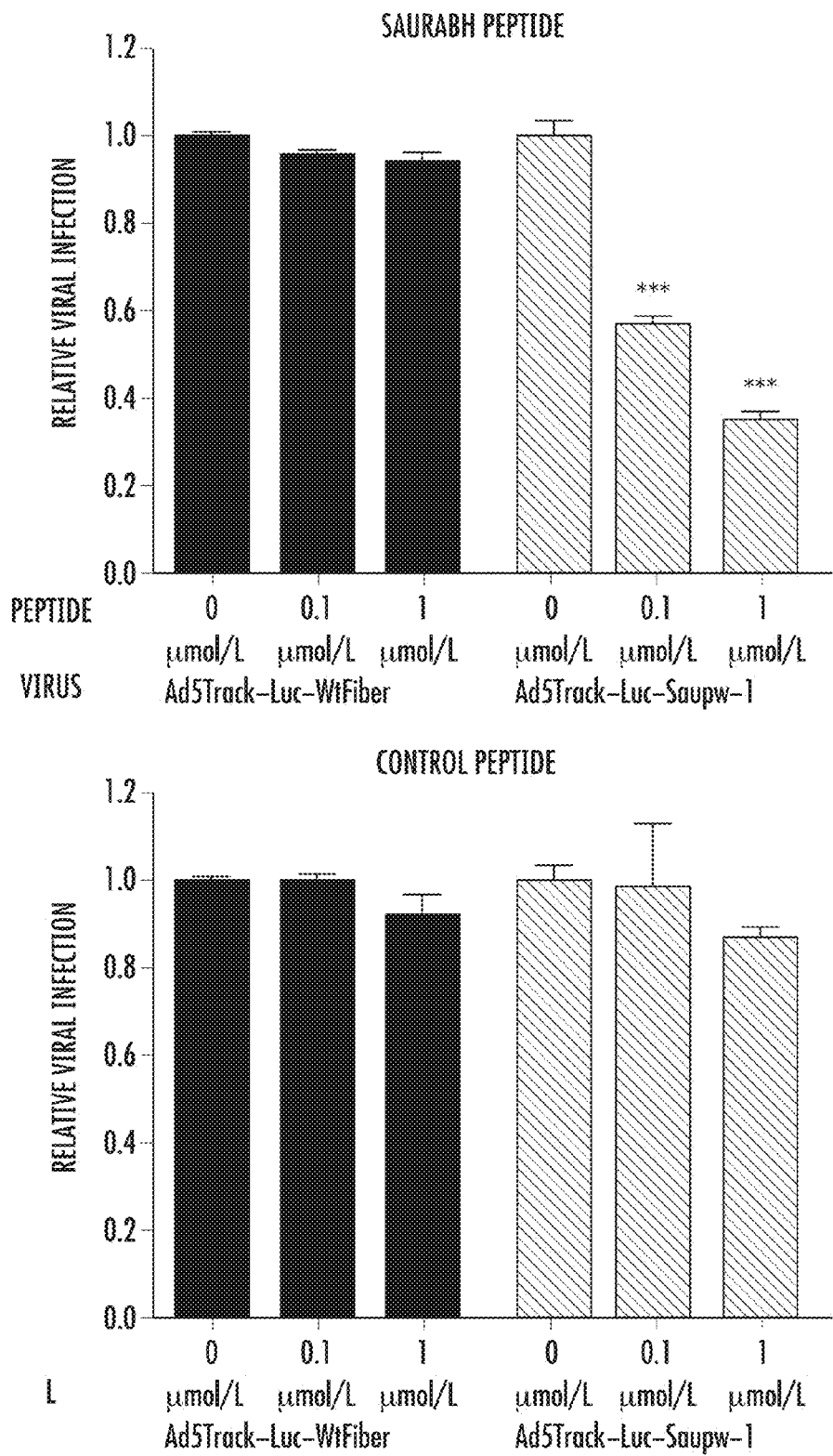
Figure 5:
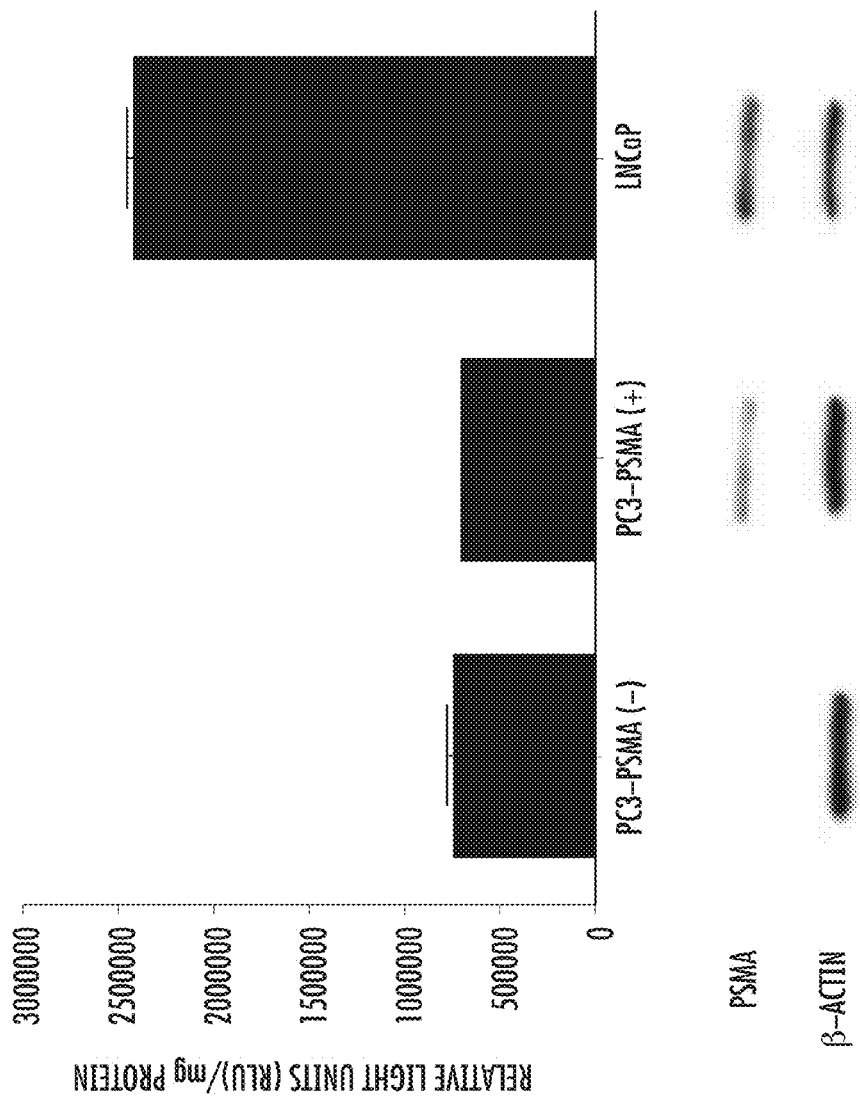
FIG. 5 shows PSMA expression models and wild type viral infection. LNCaP, PC-3-PSMA (+) and PC-3-PSMA (−) monolayers (96 well plate) were infected with Ad5Track-Luc-WtFiber (MOI=1). After about one hour, infectious media was replaced with complete medium. Luciferase activity was quantified 48 h post-infection. For western blotting, LNCaP, PC-3-PSMA (+) and PC-3-PSMA (−) cells were collected and washed twice with PBS and incubated on ice for 10 min in lysis buffer. The cell lysates were clarified by centrifugation and the supernatant protein concentrations were measured. Protein extracts were analyzed by western blotting with anti-PSMA antibody, 7E11, (1:10000 dilution), and anti-β-actin antibody (loading control). Immunoreactivity was determined by using ECL western blotting detection system.

Reporter adenovirus displaying the in vivo selected peptide Saupw-1 or the original nonflanked peptide WQPDTAHHWATL (SEQ ID NO:9) were evaluated for PSMA-mediated infection on 3 cell lines expressing varying levels of PSMA (FIG. 5). Infection rate of the selected virus Ad5Track-Luc-Saupw-1 directly correlated with PSMA expression levels in these cells, whereas the virus-displayed parental peptide Ad5Track-Luc-Saurabh showed poor infection efficiency in all 3 cell lines (FIG. 3A). Infection of adenovirus with wild-type fiber, Ad5Track-Luc-WtFiber, correlated with CAR expression and failed to show any PSMA selectivity (FIG. 5). These results indicate that the infection of Ad5Track-Luc-Saupw-1 is CAR independent and mediated by the peptide. To confirm this, competition experiments were conducted with PSMA-targeting or control peptides. AdTrack-Luc-Saupw-1 was dose-dependently inhibited by the PSMA-targeting peptide. (FIG. 3B) but not the control peptide. On the other hand, PSMA-targeting and control peptides had no effect on infection by wild-type fiber. These results support PSMA-targeted infection mediated through the Fiber-displayed peptide. Similar inhibition studies with a peptide, containing the flanking regions, did not show an increased ability to inhibit viral infection (data not shown), indicating that the selected flanking peptides enhanced folding and display rather than peptide binding affinity. Interestingly, more than 75% of the flanking sequences identified in each round contained at least 1 proline residue, which suggests that peptides in the HI-loop may be constrained or interfere with proper fiber folding and assembly. This was not only unique to the PSMA-targeting peptide but was also seen in other library selections.

Figure 3C:
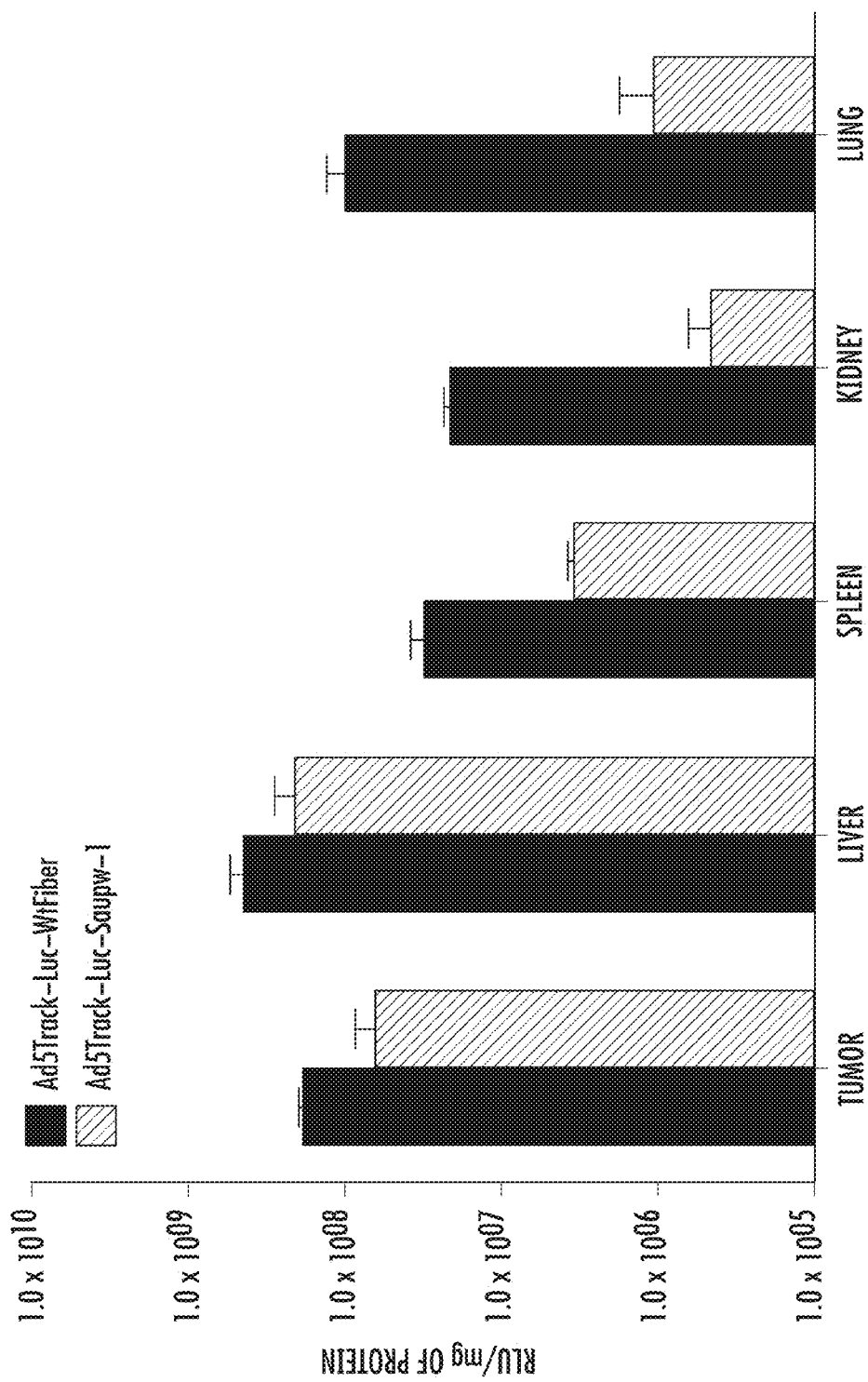
Figures 4A, 4B, 4C:
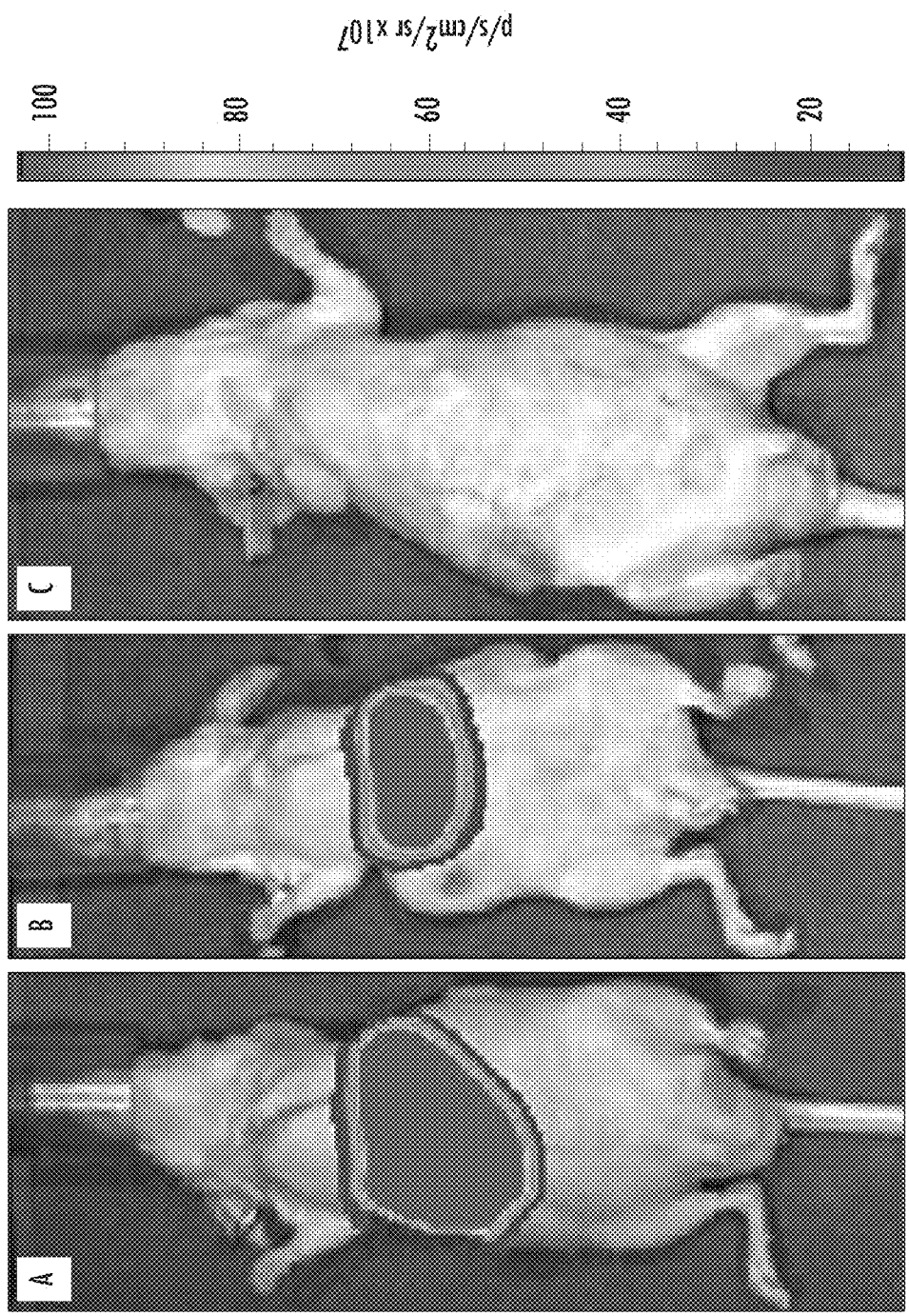
FIG. 4 shows luminescent imaging of viral infection and biodistribution. Subcutaneous LNCaP tumors were prepared in nude mice. When the tumors reached approximately 0.8 cm³ in dimension, $10^9$ IU per mouse of (A) Ad5Track-Luc-WtFiber, (B) Ad5Track-Luc-Saupw-1, or (C) PBS was administered by tail-vein injection into mice. Three days after virus injection, mice were anesthetized and imaged.

The ability of the selected virus to infect tumors in vivo after intravenous injection was then evaluated. Adenovirus biodistribution is complex and affected by many factors. In murine tissues, adenoviral biodistribution is independent of CAR binding. A series of pioneering articles recently revealed that hepatic infection is mediated by interactions between the viral hexon protein and blood factor X. See Kalyuzhniy et al., 105 PROC. NATL. ACAD. SCI. U.S.A. 5483-88 (2008); VIGANT ET AL., 16 Mol. Ther. 1474-80 (2008); and Waddington et al., 132 CELL 397-409 (2008). Indeed, hexon gene modification or blockade can reduce hepatic infection and viral induced hepatic toxicity. Shashkova et al., 17 MOL. THER. 2121-30 (2009); and Waddington et al., 132 CELL 397-409 (2008). However, the majority of injected adenovirus still remains in the liver through noninfectious sequestration. Di Paolo et al., 17 MOL. THER. 675-84 (2009). Interestingly, although CAR is not the dominant receptor for hepatic infection, it remains important in tumor models. Tumor models that express low levels of CAR are poorly infected by Ad5 vectors after systemic injection; however, infection can be rescued by the use of alternate serotype Fiber genes. The present inventors discovered that the selected PSMA-targeting peptide was capable of rescuing CAR-independent infection of LNCaP tumors (FIG. 3C). Following intravenous administration of Ad5Track-Luc-Saupw-1 ($10^9$ IU), LNCaP tumors were infected with similar efficiency when compared with adenovirus with wild-type fiber (FIG. 3C). These results reflect efficient retargeting by the PSMA-binding peptide. As expected, both virus presented significant liver transduction (FIG. 3C), as confirmed by in vivo luciferase imaging (FIG. 4). Transgene expression in tumor xenografts could not be observed from bioluminescence imaging with either wild-type or PSMA-targeted Fiber genes, which is generally expected following systemic administration of replication-incompetent adenovirus reporters. On the other hand, Ad5Track-Luc-Saupw-1 infected kidney and lung with significantly lower efficiency. These results are consistent with previous studies utilizing $Y_{477}A$ detargeting mutations. See Bayo-Puxan et al., 87 J. GEN. VIROL. 2487-95 (2006). Therefore, the combination of CAR detargeting and PSMA retargeting has affected the systemic infection pattern of the virus in some tissues while still retaining efficient tumor cell infection (FIG. 2D).

REFERENCES

1. Waehler et al., 8 NAT. REV. GENET. 573-87 (2007).
2. Barry et al., 11 CURR. OPIN. MOL. THER. 411-20 (2009).
3. Rodriguez et al., 57 CANCER RES. 2559-63 (1997).
4. Lupold et al., 3 CANCER THER. 267-84 (2005).
5. Shashkova et al., 17 MOL. THER. 2121-30 (2009).
6. Ghosh et al., 79 J. VIROL. 13667-72 (2005).
7. Lupold et al., 35 NUCLEIC ACIDS RES. e138 (2007).
8. Miura et al., 14 GENE THER. 1448-60 (2007).
9. Elgamal et al., 18 SEMIN. SURG. ONCOL. 10-16 (2000).
10. Chen et al., 51 J. MED. CHEM. 7933-43 (2008).
11. Aggarwal et al., 66 CANCER RES. 9171077 (2006).
12. Rege et al., 67 CANCER RES. 6368-75 (2007).
13. Hoti et al., 17 CANCER GENE THER. 1-13 (2010).
14. Peng et al., 354 ANAL. BIOCHEM. 140-47 (2006).
15. Roelvink et al., 286 SCIENCE 1568-71 (1999).
16. Waddington et al., 132 CELL 397-409 (2008).
17. Kalyuzhniy et al., 105 PROC. NATL. ACAD. SCI. U.S.A. 5483-88 (2008).
18. Vigant et al., 16 MOL. THER. 1474-80 (2008).
19. Di Paolo et al., 17 MOL. THER. 675-84 (2009).
20. Bayo-Puxan et al., 87 J. GEN. VIROL. 2487-95 (2006).
21. Alemany et al., 8 GENE THER. 1347-53 (2001)
22. Shayakhmetov et al., 79 J. VIROL. 7478-91 (2005).

We claim:

1. A method for optimizing infection of target cells by an adenovirus displaying an antigen targeting peptide comprising the steps of:
   a. selecting an antigen targeting peptide to be displayed in an adenovirus, wherein the displayed targeting peptide is a peptide that specifically binds an antigen expressed on the surface of a target cell;
   b. generating peptide-display adenovirus library that displays the selected antigen targeting peptide of step (a), wherein the amino acid sequence encoding the displayed antigen targeting peptide is flanked by random peptide sequences; and
   c. screening the antigen targeting peptide-display adenovirus library against the target cells to isolate adenovirus that optimally infects the target cells.

2. The method of claim 1, wherein one or both of the flanking random peptide sequences are selected from the group consisting of a monomer, a dimer, a trimer, a tetramer, a pentamer, a hexamer, a septamer, a octamer, and a nonamer.

3. The method of claim 1, wherein the flanking random peptide sequences are multimers.

4. The method of claim 1, wherein the flanking random peptide sequences are trimers.

5. The method of claim 1, wherein the target cell is a cancer cell.

* * * * *

SEQUENCE LISTING

<160> NUMBER OF SEQ ID NOS: 46

<210> SEQ ID NO 1
<211> LENGTH: 35
<212> TYPE: DNA
<213> ORGANISM: Artificial Sequence
<220> FEATURE:
<223> OTHER INFORMATION: Primer BFB-1 for site mutation Y477A in
      adenovirus

<400> SEQUENCE: 1
cttcctggac ccagaagctt ggaactttag aaatg                              35

<210> SEQ ID NO 2
<211> LENGTH: 35
<212> TYPE: DNA
<213> ORGANISM: Artificial Sequence
<220> FEATURE:
<223> OTHER INFORMATION: Primer BFB-2 for site mutation Y477A in
      adenovirus

<400> SEQUENCE: 2
catttctaaa gttccaagct tctgggtcca ggaag                              35

<210> SEQ ID NO 3
<211> LENGTH: 17
<212> TYPE: DNA
<213> ORGANISM: Artificial Sequence
<220> FEATURE:
<223> OTHER INFORMATION: M13 forward primer

<400> SEQUENCE: 3
gtaaaacgac ggccagt                                                  17

<210> SEQ ID NO 4
<211> LENGTH: 19
<212> TYPE: DNA
<213> ORGANISM: Artificial Sequence
<220> FEATURE:
<223> OTHER INFORMATION: M13 reverse primer

<400> SEQUENCE: 4
ggaaacagct atgaccatg                                                19

<210> SEQ ID NO 5
<211> LENGTH: 20
<212> TYPE: DNA
<213> ORGANISM: Artificial Sequence
<220> FEATURE:
<223> OTHER INFORMATION: Fiber-S2 primer

<400> SEQUENCE: 5
ctcaccccct ctaactactg                                               20

<210> SEQ ID NO 6
<211> LENGTH: 20
<212> TYPE: DNA
<213> ORGANISM: Artificial Sequence
<220> FEATURE:
<223> OTHER INFORMATION: Fiber-S3 primer

<400> SEQUENCE: 6
caggagatgg gcttgaattt                                               20

<210> SEQ ID NO 7
<211> LENGTH: 96

```
<212> TYPE: DNA
<213> ORGANISM: Artificial Sequence
<220> FEATURE:
<223> OTHER INFORMATION: oligonucleotide library template 5' biotin
      primer
<220> FEATURE:
<221> NAME/KEY: misc_feature
<222> LOCATION: (1)..(96)
<223> OTHER INFORMATION: n=a, g, c or t
<220> FEATURE:
<221> NAME/KEY: misc_feature
<222> LOCATION: (1)..(96)
<223> OTHER INFORMATION: m=c or a

<400> SEQUENCE: 7
tggagttgtg tctccggamn nmnnmnncag tgttgcccag tggtgtgcgg tatcaggctg      60
ccamnnmnnm nngaattcgg attcctgtgt accgct                                96

<210> SEQ ID NO 8
<211> LENGTH: 16
<212> TYPE: DNA
<213> ORGANISM: Artificial Sequence
<220> FEATURE:
<223> OTHER INFORMATION: Extension primer Lib001 5' Biotin

<400> SEQUENCE: 8
agcggtacag gaatcc                                                     16

<210> SEQ ID NO 9
<211> LENGTH: 12
<212> TYPE: PRT
<213> ORGANISM: Artificial Sequence
<220> FEATURE:
<223> OTHER INFORMATION: PSMA-targeting peptide

<400> SEQUENCE: 9

Trp Gln Pro Asp Thr Ala His His Trp Ala Thr Leu
1               5                   10

<210> SEQ ID NO 10
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 10

Met Ala Glu Trp Gln Pro Asp Thr Ala His His Trp Ala Thr Leu Pro
1               5                   10                  15

Asp Pro

<210> SEQ ID NO 11
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 11

Pro Thr Pro Trp Gln Pro Asp Thr Ala His His Trp Ala Thr Leu Pro
1               5                   10                  15

Thr Arg

<210> SEQ ID NO 12
```

```
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 12

Pro Met Asn Trp Gln Pro Asp Thr Ala His His Trp Ala Thr Leu Ile
1               5                   10                  15

Thr Asp

<210> SEQ ID NO 13
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 13

Ser Pro Ala Trp Gln Pro Asp Thr Ala His His Trp Ala Thr Leu Ser
1               5                   10                  15

Ser His

<210> SEQ ID NO 14
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 14

Pro Pro Pro Trp Gln Pro Asp Thr Ala His His Trp Ala Thr Leu Pro
1               5                   10                  15

Asn Ile

<210> SEQ ID NO 15
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 15

Pro Glu Thr Trp Gln Pro Asp Thr Ala His His Trp Ala Thr Leu Gly
1               5                   10                  15

Thr Pro

<210> SEQ ID NO 16
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 16

Tyr Lys Pro Trp Gln Pro Asp Thr Ala His His Trp Ala Thr Leu Ser
1               5                   10                  15

His Gln
```

```
<210> SEQ ID NO 17
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 17

Ser Pro Arg Trp Gln Pro Asp Thr Ala His His Trp Ala Thr Leu Thr
1               5                   10                  15

Ser Pro

<210> SEQ ID NO 18
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 18

Thr Arg Pro Trp Gln Pro Asp Thr Ala His His Trp Ala Thr Leu Pro
1               5                   10                  15

His Thr

<210> SEQ ID NO 19
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 19

Thr Ser Pro Trp Gln Pro Asp Thr Ala His His Trp Ala Thr Leu Ser
1               5                   10                  15

Lys Arg

<210> SEQ ID NO 20
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 20

Asp Lys Met Trp Gln Pro Asp Thr Ala His His Trp Ala Thr Leu His
1               5                   10                  15

Pro Phe

<210> SEQ ID NO 21
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 21

Asn Ser Arg Trp Gln Pro Asp Thr Ala His His Trp Ala Thr Leu Thr
1               5                   10                  15

Thr Arg
```

```
<210> SEQ ID NO 22
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 22

Pro Ser Thr Trp Gln Pro Asp Thr Ala His His Trp Ala Thr Leu Pro
1               5                   10                  15

His Leu

<210> SEQ ID NO 23
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 23

Pro Ser Leu Trp Gln Pro Asp Thr Ala His His Trp Ala Thr Leu Tyr
1               5                   10                  15

Pro Met

<210> SEQ ID NO 24
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 24

Leu Ala Pro Trp Gln Pro Asp Thr Ala His His Trp Ala Thr Leu Thr
1               5                   10                  15

Asp Thr

<210> SEQ ID NO 25
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 25

Thr Ser Asn Trp Gln Pro Asp Thr Ala His His Trp Ala Thr Leu Ala
1               5                   10                  15

Cys Thr

<210> SEQ ID NO 26
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 26

Asn Pro Ser Trp Gln Pro Asp Thr Ala His His Trp Ala Thr Leu Lys
1               5                   10                  15

Asn Gln
```

<210> SEQ ID NO 27
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 27

Pro Thr Asn Trp Gln Pro Asp Thr Ala His His Trp Ala Thr Leu Met
1               5                   10                  15

Pro Ser

<210> SEQ ID NO 28
<211> LENGTH: 17
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 28

Ser Asn Tyr Trp Gln Pro Asp Thr Ala His His Trp Ala Thr Leu Pro
1               5                   10                  15

Asn

<210> SEQ ID NO 29
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 29

Cys Thr Asn Trp Gln Pro Asp Thr Ala His His Trp Ala Thr Leu Lys
1               5                   10                  15

Asp Ser

<210> SEQ ID NO 30
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 30

Tyr Asn Ser Trp Gln Pro Asp Thr Ala His His Trp Ala Thr Leu Pro
1               5                   10                  15

Thr Ala

<210> SEQ ID NO 31
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 31

Thr Arg Glu Trp Gln Pro Asp Thr Ala His His Trp Ala Thr Leu Asp
1               5                   10                  15

Ser Ser

<210> SEQ ID NO 32
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 32

Gly Gln Ser Trp Gln Pro Asp Thr Ala His His Trp Ala Thr Leu Glu
1               5                   10                  15

Glu Thr

<210> SEQ ID NO 33
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 33

Ser Gly Val Trp Gln Pro Asp Thr Ala His His Trp Ala Thr Leu Lys
1               5                   10                  15

Thr Pro

<210> SEQ ID NO 34
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 34

Ala Gly Asp Trp Gln Pro Asp Thr Ala His His Trp Ala Thr Leu Lys
1               5                   10                  15

Ala Asp

<210> SEQ ID NO 35
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 35

Ser Gln Thr Trp Gln Pro Asp Thr Ala His His Trp Ala Thr Leu Pro
1               5                   10                  15

Trp Pro

<210> SEQ ID NO 36
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 36

Gly Gly Pro Trp Gln Pro Asp Thr Ala His His Trp Ala Thr Leu Pro
1               5                   10                  15

Asn Ser

<210> SEQ ID NO 37
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 37

Val His Arg Trp Gln Pro Asp Thr Ala His His Trp Ala Thr Leu Asn
1               5                   10                  15

Arg Gln

<210> SEQ ID NO 38
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 38

Pro Pro Lys Trp Gln Pro Asp Thr Ala His His Trp Ala Thr Leu Pro
1               5                   10                  15

Pro Pro

<210> SEQ ID NO 39
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 39

Leu Pro Thr Trp Gln Pro Asp Thr Ala His His Trp Ala Thr Leu Asp
1               5                   10                  15

Ser Glu

<210> SEQ ID NO 40
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 40

Pro Asn Val Trp Gln Pro Asp Thr Ala His His Trp Ala Thr Leu Pro
1               5                   10                  15

Tyr Pro

<210> SEQ ID NO 41
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 41

Glu Pro Cys Trp Gln Pro Asp Thr Ala His His Trp Ala Thr Leu Pro

```
                1               5                  10                  15
Glu Ile

<210> SEQ ID NO 42
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 42

Ala Lys Asp Trp Gln Pro Asp Thr Ala His His Trp Ala Thr Leu Asp
1               5                  10                  15

Asn Val

<210> SEQ ID NO 43
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 43

Pro Ala Ser Trp Gln Pro Asp Thr Ala His His Trp Ala Thr Leu Pro
1               5                  10                  15

Gln Arg

<210> SEQ ID NO 44
<211> LENGTH: 18
<212> TYPE: PRT
<213> ORGANISM: Artificial Sequence
<220> FEATURE:
<223> OTHER INFORMATION: PSMA-targeting peptide flanked by 3 random
      amino acid cassettes

<400> SEQUENCE: 44

Pro Arg Pro Trp Gln Pro Asp Thr Ala His His Trp Ala Thr Leu Pro
1               5                  10                  15

Arg Gln

<210> SEQ ID NO 45
<211> LENGTH: 18
<212> TYPE: PRT
<213> ORGANISM: Artificial Sequence
<220> FEATURE:
<223> OTHER INFORMATION: Peptide sequence wherein X is an antigen
      targeting peptide
<220> FEATURE:
<221> NAME/KEY: MISC_FEATURE
<222> LOCATION: (4)..(15)
<223> OTHER INFORMATION: Any one or all of amino acids 4-15 can be
      present or absent.

<400> SEQUENCE: 45

Met Ala Glu Xaa Xaa Xaa Xaa Xaa Xaa Xaa Xaa Xaa Xaa Xaa Xaa Pro
1               5                  10                  15

Asp Pro

<210> SEQ ID NO 46
<211> LENGTH: 4
<212> TYPE: PRT
<213> ORGANISM: Artificial Sequence
<220> FEATURE:
```

-continued

```
<223> OTHER INFORMATION: Generation of fiber-shuttle plasmid for the
      Coxsackie and Adenovirus Receptor (CAR) binding ablation by
      deletion of amino acids T489AYT492 in the FG loop has been
      described previously. See Lupold et al., 35 NUCLEIC ACIDS RES.
      e138 (2007).

<400> SEQUENCE: 46

Thr Ala Tyr Thr
1
```